US009681993B2

(12) United States Patent
Wu et al.

(10) Patent No.: US 9,681,993 B2
(45) Date of Patent: Jun. 20, 2017

(54) SOLUTIONS FOR BRIDGING AND PRESSURE CONCENTRATION REDUCTION AT WOUND SITES

(75) Inventors: Kenneth Wu, San Francisco, CA (US); Darren Ng, Redwood City, CA (US); Jennifer Lee, San Francisco, CA (US); Dean Hu, San Leandro, CA (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 13/490,844

(22) Filed: Jun. 7, 2012

(65) Prior Publication Data

US 2013/0144230 A1    Jun. 6, 2013

Related U.S. Application Data

(60) Provisional application No. 61/494,367, filed on Jun. 7, 2011.

(51) Int. Cl.
*A61M 27/00* (2006.01)
*A61M 25/00* (2006.01)
(Continued)

(52) U.S. Cl.
CPC .... *A61F 13/0216* (2013.01); *A61F 13/00068* (2013.01); *A61M 1/0027* (2014.02);
(Continued)

(58) Field of Classification Search
CPC ... A61M 1/008; A61M 1/0088; A61M 1/0094
See application file for complete search history.

(56) References Cited

U.S. PATENT DOCUMENTS 4,553,967 A    11/1985 Ferguson et al.
4,759,354 A    7/1988 Quarfoot
(Continued)

FOREIGN PATENT DOCUMENTS

WO    2006/025848 A2    3/2006
WO    2006/025848 A3    10/2006
(Continued)

OTHER PUBLICATIONS

"Brava Strip Paste". Coloplast. <http://www.coloplast.us/brava-strip-paste-en-us.aspx#section=product-description_3>. Jun. 5, 2013. See attached NPL.*
(Continued)

*Primary Examiner* — Tatyana Zalukaeva
*Assistant Examiner* — Sara Sass

(57) ABSTRACT

Disclosed herein are devices, systems and methods for delivering reduced pressure to a load-bearing wound site. The device can include a distal port configured to connect to a wound dressing positioned over the wound site; a proximal port located a distance from the distal port and configured to connect to a reduced pressure source, and a conduit body having an inner channel extending between the distal port and the proximal port. When the distal port is applied to the wound dressing positioned over the wound site the proximal port is positioned at a non-load bearing location remote from the wound dressing. The inner channel has a non-circular profile having a width larger than a height of the conduit body.

25 Claims, 27 Drawing Sheets

(51) Int. Cl.
*A61F 13/68* (2006.01)
*A61F 13/02* (2006.01)
*A61M 1/00* (2006.01)
*A61F 13/00* (2006.01)

(52) U.S. Cl.
CPC ........ *A61M 1/0086* (2014.02); *A61M 1/0088* (2013.01); *A61F 2013/00174* (2013.01); *A61F 2013/00412* (2013.01); *A61F 2013/00536* (2013.01)

(56) References Cited

U.S. PATENT DOCUMENTS

| | | | |
|---|---|---|---|
| 6,071,267 A | | 6/2000 | Zamierowski |
| 6,306,485 B1 | | 10/2001 | Keller |
| 7,815,616 B2 | | 10/2010 | Boehringer et al. |
| 7,942,866 B2 | | 5/2011 | Radl et al. |
| 8,083,712 B2 | | 12/2011 | Biggie et al. |
| 8,128,607 B2 | | 3/2012 | Hu et al. |
| 8,158,844 B2 | | 4/2012 | McNeil |
| 8,162,907 B2 | | 4/2012 | Heagle |
| 8,409,156 B2 | | 4/2013 | Kazala, Jr. et al. |
| 2005/0101940 A1* | | 5/2005 | Radl et al. ............ 604/543 |
| 2007/0016152 A1* | | 1/2007 | Karpowicz et al. ........ 604/326 |
| 2007/0066945 A1* | | 3/2007 | Martin ............ A61M 1/0058 604/313 |
| 2007/0185426 A1 | | 8/2007 | Ambrosio et al. |
| 2008/0108977 A1 | | 5/2008 | Heaton et al. |
| 2008/0167593 A1 | | 7/2008 | Fleischmann |
| 2008/0294147 A1 | | 11/2008 | Radl et al. |
| 2009/0012482 A1* | | 1/2009 | Pinto ............ A61F 13/00029 604/313 |
| 2009/0227969 A1* | | 9/2009 | Jaeb ............ A61M 1/0088 604/313 |
| 2009/0234264 A1 | | 9/2009 | Randolph |
| 2009/0312728 A1 | | 12/2009 | Randolph et al. |
| 2010/0087767 A1 | | 4/2010 | McNeil |
| 2010/0137775 A1 | | 6/2010 | Hu et al. |
| 2010/0160877 A1* | | 6/2010 | Kagan ............ A61M 1/0023 604/319 |
| 2010/0174250 A1 | | 7/2010 | Hu et al. |
| 2010/0185163 A1 | | 7/2010 | Heagle |
| 2010/0210986 A1 | | 8/2010 | Sanders et al. |
| 2010/0262126 A1 | | 10/2010 | Hu et al. |
| 2013/0090615 A1 | | 4/2013 | Jaeb et al. |

FOREIGN PATENT DOCUMENTS

| | | |
|---|---|---|
| WO | 2010/042240 A1 | 4/2010 |
| WO | 2010/085270 A1 | 7/2010 |

OTHER PUBLICATIONS

"Coloplast Brava Strip Paste". Coloplast. <http://www.coloplastus/brava-strip-paste-en-us.aspx#section=product-description_3>. Jun. 20, 2015. See attached.*
International Search Report received for PCT Patent Application No. PCT/US2012/041432, mailed on Nov. 20, 2012, 4 pages.
Armstrong et al., "Decreasing Foot Pressures While Implementing Topical Negative Pressure (Vacuum-Assisted Closure) Therapy", Lower Extremity Wounds, vol. 3, No. 1, 2004, pp. 12-15.
Greer et al., "Techniques for Applying Subatmospheric Pressure Dressing to Wounds in Difficult Regions of Anatomy", JWOCN, vol. 26, No. 5, Sep. 1999, pp. 250-253.
Innovative Therapies Inc.,"Delivering Negative Pressure Wound Therapy (NPWT) to Multiple Wounds", ITI Bridging Set, 2011, 2 pages.
KCI V.A.C.° Therapy Systems, "V.A.C.° Therapy System Safety Information and V.A.C.° GranuFoam TM Bridge Dressing Application Instructions", 330900 Rev C, May 2009, 240 pages.
Pryor III et al., "Wound VAC for Fournier's Gangrene: A New Technique for Applying a Vacuumassisted Closure Device on Multiple Wound Sites using Minimal Connectors", OPUS 12 Scientist 2009, vol. 3, No. 3, 2009, pp. 47-49.
Rock, Ronald, "Get Positive Results with Negative-Pressure Wound Therapy", American Nurse Today, vol. 6, No. 1, Jan. 2011, pp. 49-51.
International Preliminary Report on Patentability received for PCT Patent Application No. PCT/US2012/041432, mailed on Dec. 27, 2013, 8 pages.
Written Opinion received for PCT Patent Application No. PCT/US2012/041432, mailed on Nov. 20, 2012, 6 pages.

* cited by examiner

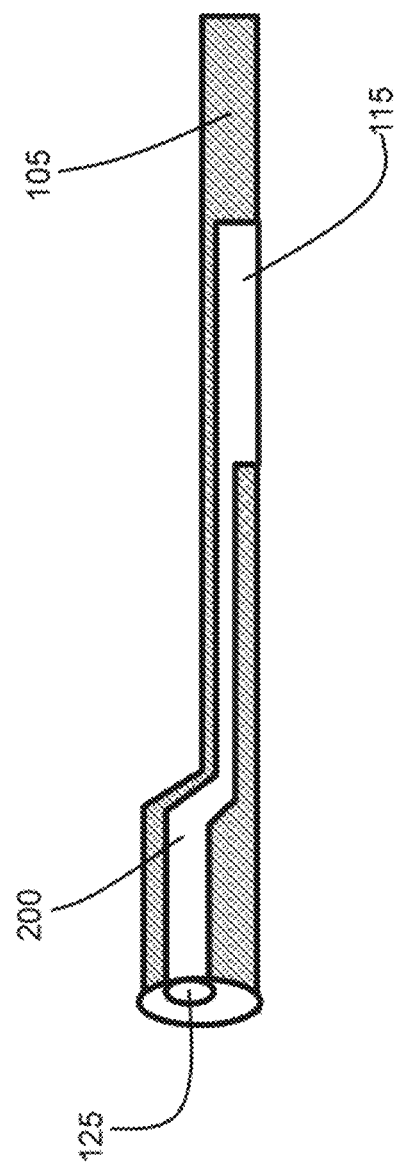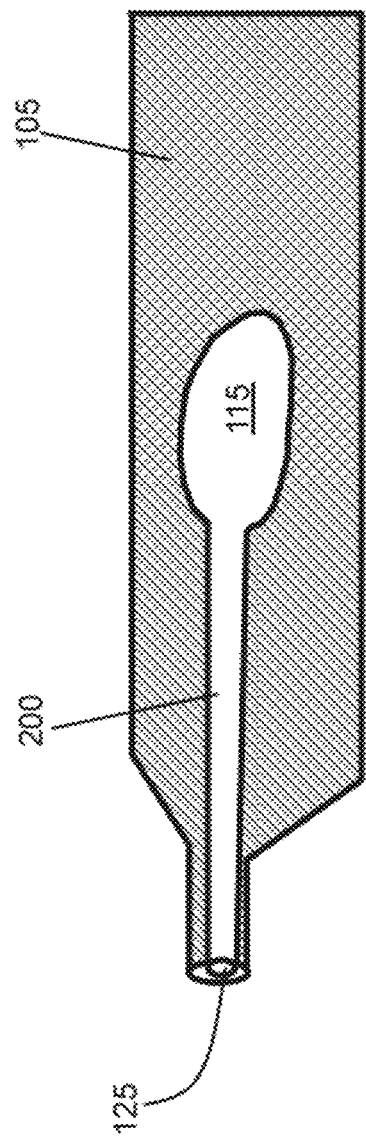
FIG. 2A
FIG. 2B

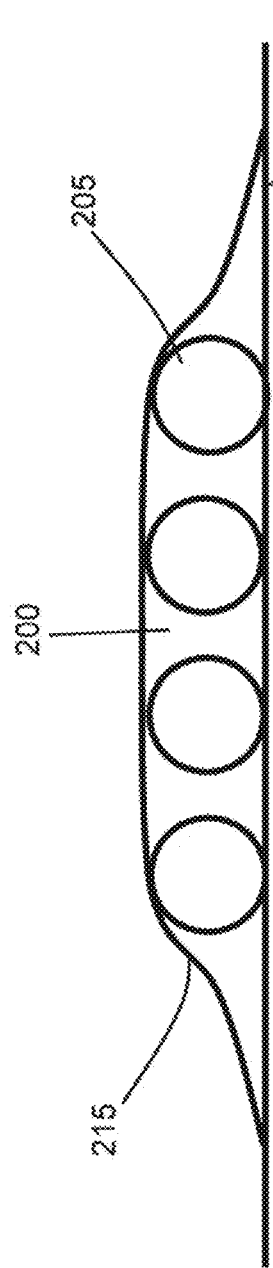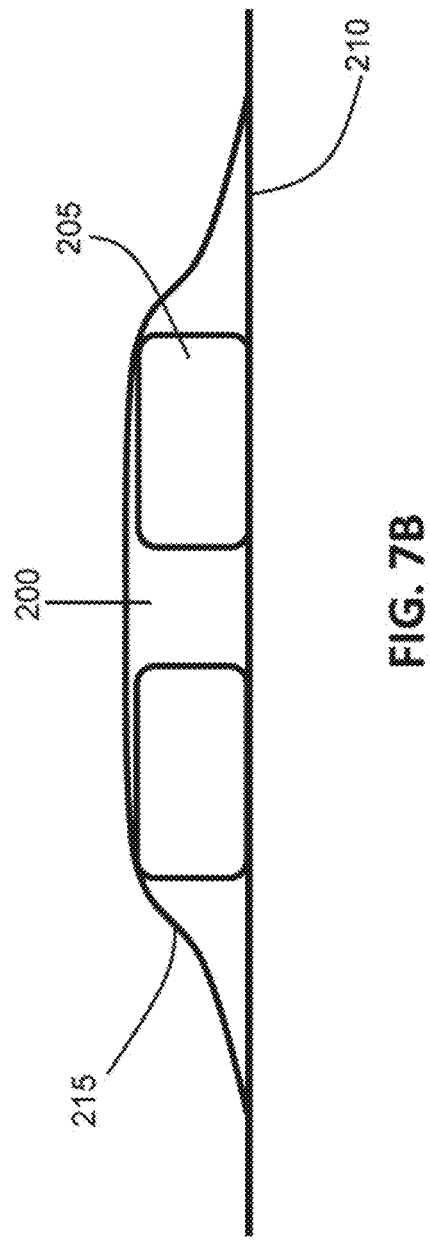

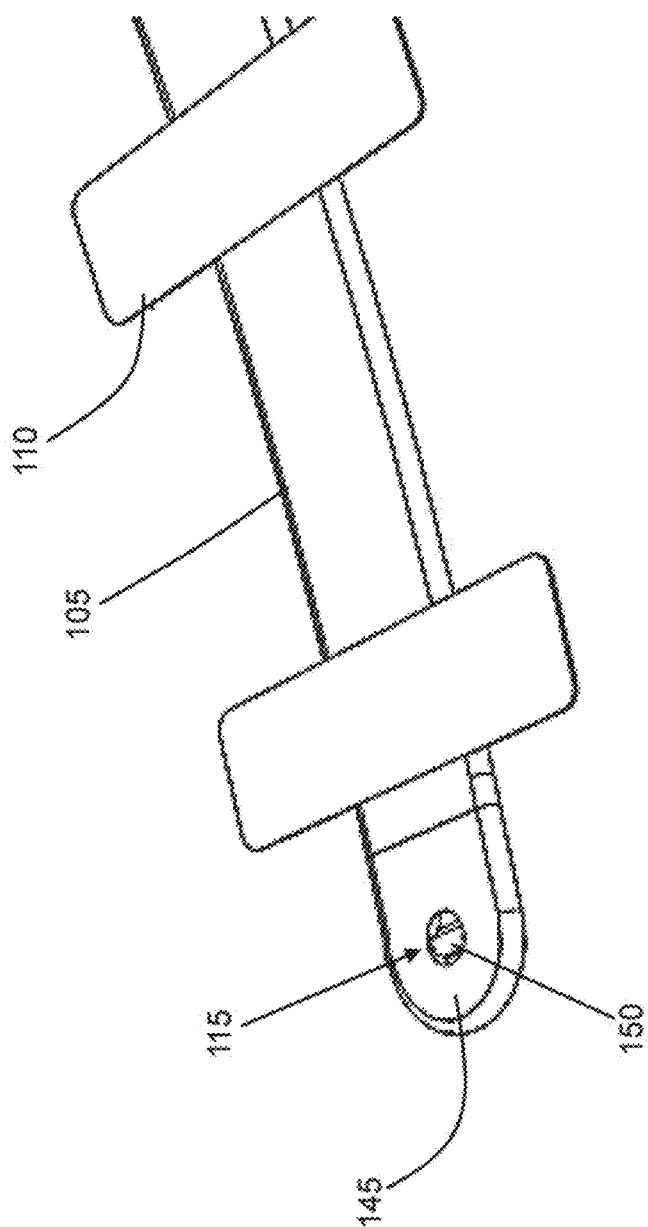

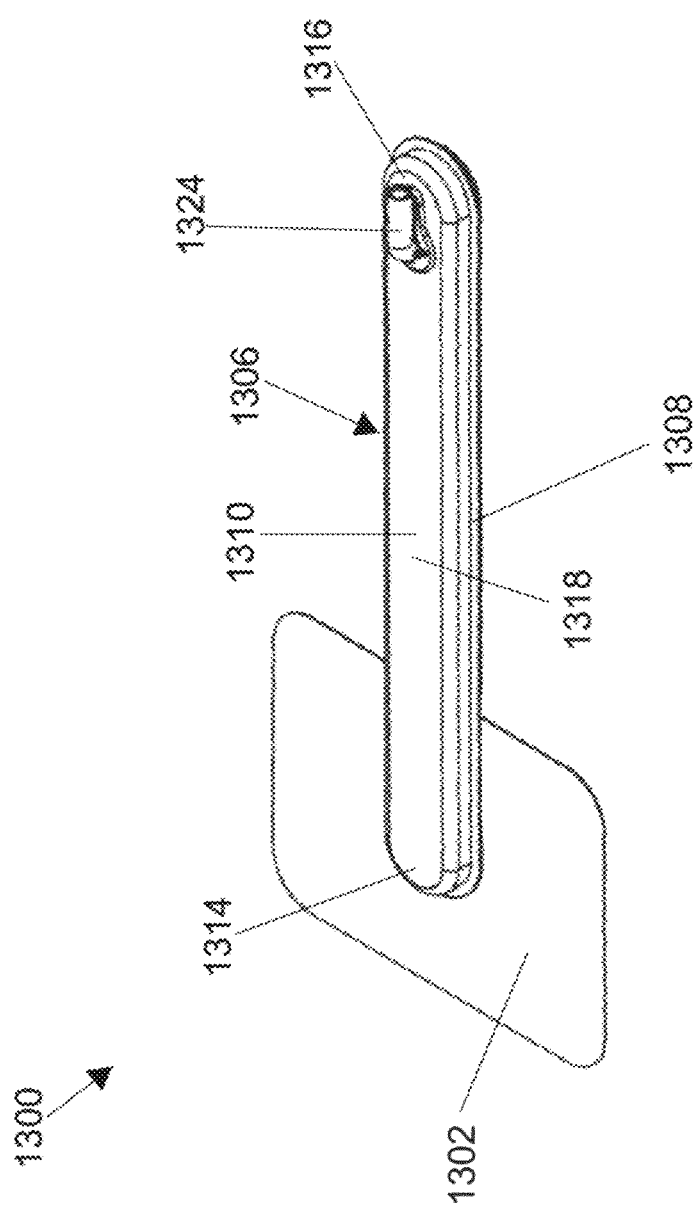

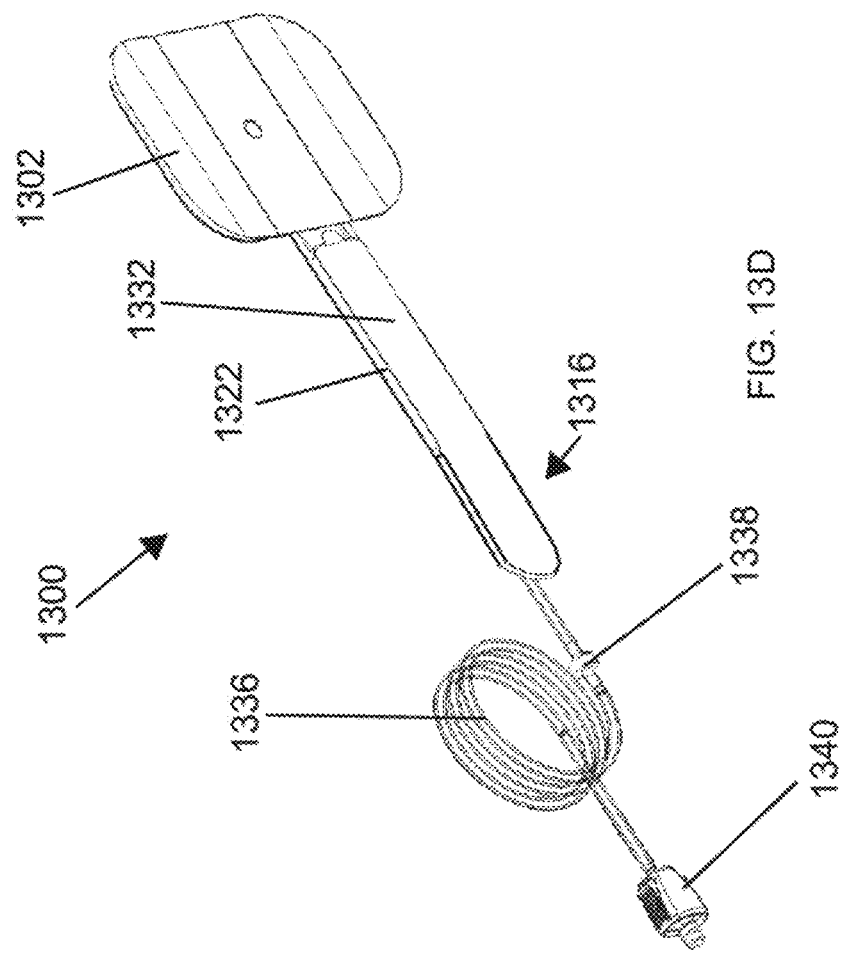

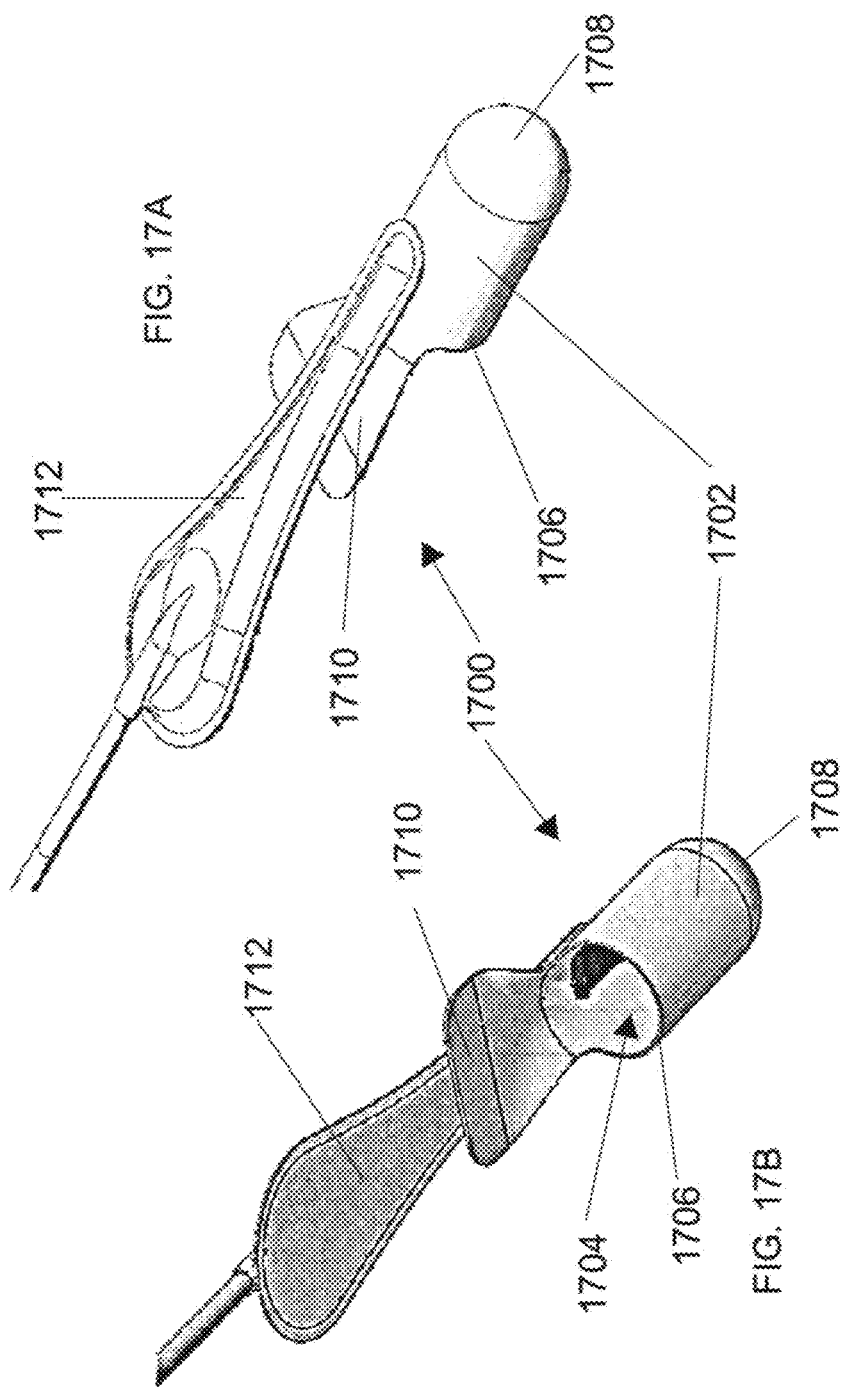

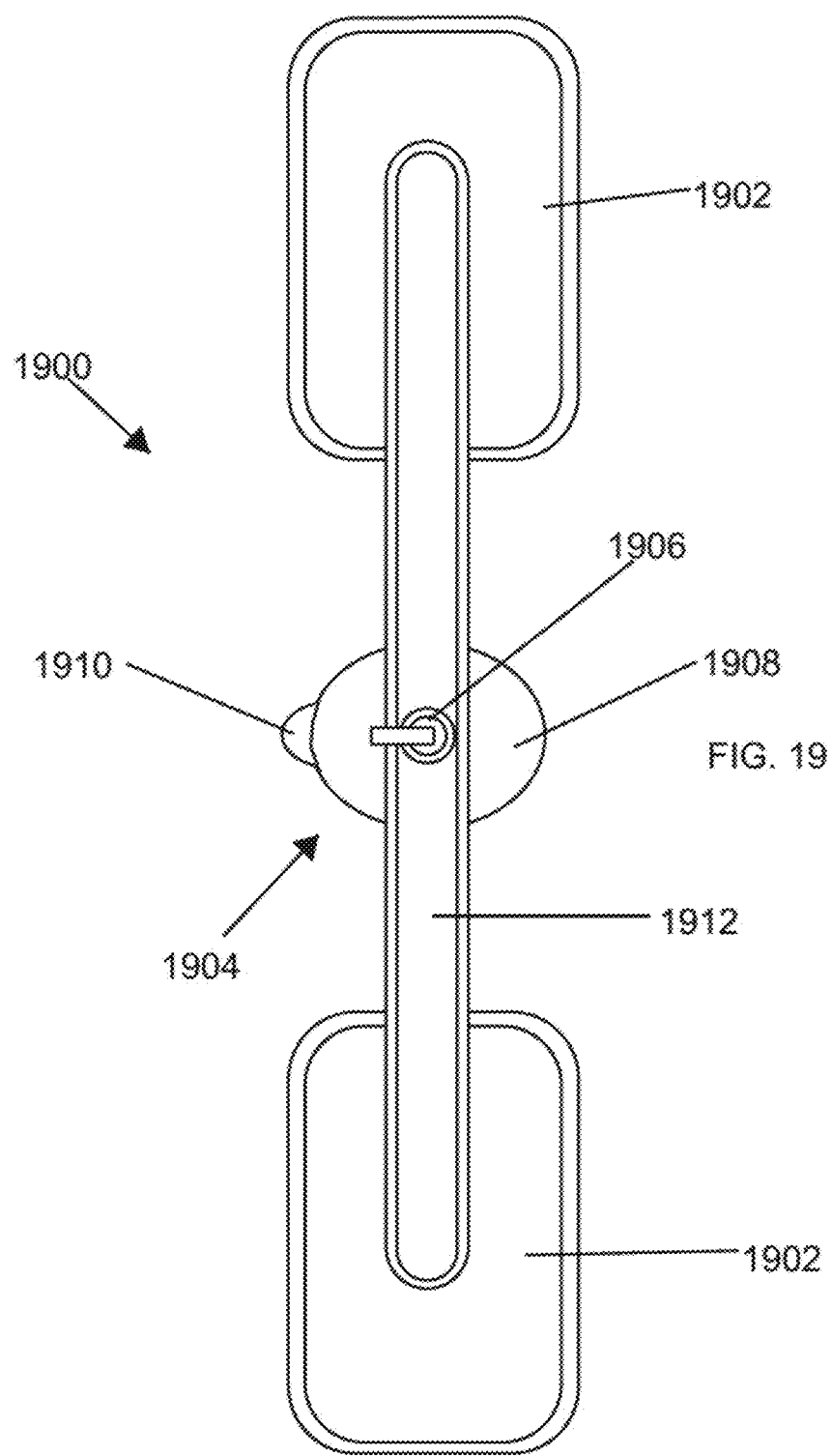

SOLUTIONS FOR BRIDGING AND PRESSURE CONCENTRATION REDUCTION AT WOUND SITES

CROSS-REFERENCE TO RELATED APPLICATIONS

This application claims benefit under 35 U.S.C. §119(e) to U.S. Provisional Application Ser. No. 61/494,367, filed on Jun. 7, 2011, which is hereby incorporated by reference in their entirety.

BACKGROUND

Pressure sores or decubitus ulcers classically result from localized tissue ischemia at pressure points on a patient's skin associated with immobility. However, friction and maceration at the skin site may also be contributing factors. Common locations of decubitus ulcers include the heel, the ankle, the sacral region, the coccygeal region, the ischial region, the knee, and the elbow. Traditional therapy for pressure ulcers has focused on prevention of these ulcers, due to the difficulty of treating the ulcers once they have formed. These treatments include nursing protocols to frequently turn or change the position of bedbound patients, as well as equipment to redistribute focal forces acting on a patient's skin, such as foam boots and fluidized beds.

Recently, the delivery of reduced pressure wound therapy (RPWT) has shown promise in the treatment of wounds. Typically, RPWT involves creating an enclosed space around a wound and connecting this enclosed space to a reduced pressure source. The creation of the enclosed space is achieved most commonly with an adhesive-coated thin polyurethane film. A conduit, typically a port that may be connected to flexible tubing, from the enclosure created by the adhesive barrier usually is used to connect to the reduced pressure source which facilitates reduced pressure application to the wound site as well as removal of wound exudates. RPWT has been shown to accelerate or promote the healing of a variety of chronic wounds, including diabetic ulcers, venous stasis ulcers, surgical wounds and traumatic wounds.

SUMMARY

Disclosed herein are devices and methods that can be used to provide substantially airtight seal for reduced pressure wound therapy (RPWT) or negative pressure therapy (NPT) that can be configured to also accommodate the anatomic particularities of various regions typically prone to pressure point ulceration. The devices described herein may be low profile and comprise low durometer materials and can be used to bridge a pressure-prone region of the body to another region, so that any tubing and/or ports which may concentrate pressure transmission at load-bearing surfaces may be positioned remotely from the treatment site. In a first embodiment, a low-profile device for delivering reduced pressure to a load-bearing wound site is provided. The device may include a distal port configured to connect to a wound dressing positioned over the wound site; a proximal port located a distance from the distal port and configured to connect to a reduced pressure source, and a conduit body having an inner channel extending between the distal port and the proximal port. When the distal port is applied to the wound dressing positioned over the wound site the proximal port is positioned at a non-load bearing location remote from the wound dressing. The inner channel may comprise a non-circular profile having a width larger than a height of the conduit body, which may redistribute any transmitted forces across a larger surface area compared to a circular profile, thereby reducing concentrated regions of applied pressure to underlying tissue.

The device may further include a sealing layer having an adhesive lower surface configured to be adhered to the load-bearing wound site. The adhesive lower surface can include a material that absorbs moisture and maintains skin health. The conduit body can include an adhesive lower surface that prevents movement of the conduit body relative to an underlying skin surface. A junction between the adhesive lower surface of the conduit body and the adhesive lower surface of the sealing layer can include an interruption to prevent peel propagation of the conduit body to the sealing layer. A distal region of the conduit body surrounding the distal port can be coupled to an upper surface of the sealing layer. The distal region of the conduit body can be permanently coupled to the upper surface. The conduit body can include one or more support structures protruding into the channel.

The one or more support structures can mitigate collapse of the channel upon application of external pressure to the conduit body. The one or more support structures can include elongate ribs or protrusions coupled to an inner wall of the conduit body, and/or grooves or indentations in the inner wall. The conduit body can have a multi-layer construction having the one or more support structures sandwiched between an upper cover and a lower base. The one or more support structures can have a porosity sufficient to allow the delivery of reduced pressure to the wound site and the flow of fluid from the wound site through the inner channel. The support structure can be selected from the group consisting of a mesh structure, a synthetic textile, foam, fabric, non-woven fabric, silicone, urethane, cotton and gauze. The conduit body can have a first durometer and the one or more support structures can have a second durometer. The first durometer can be less than the second durometer or more than the second durometer. The one or more support structures can be arranged adjacent the distal port to evenly distribute loads and maintain patency of the distal port upon application of external pressure to the distal port. The distance of the proximal port from the distal port can have a range of about 4 inches to about 12 inches. In other variations, the distance between the ports may be from about 2 inches to about 18 inches, from about 3 inches to about 24 inches, or about 12 inches to about 36 inches. The device can further include a pressure indicator configured to indicate pressure delivered locally to the wound site. The pressure indicator may be located in a port structure of the device. The device may also further include a contact surface positioned under the conduit body, and/or a padding material located on an exterior surface of the conduit body. The device may also further comprise a low-tack adhesive located on at least a portion of the padding material configured to adhere to a patient's skin; and a release liner releasably adhered to the low-tack adhesive, wherein the release liner comprises a porous or padded material configured to contact the patient's skin.

In another embodiment, a reduced pressure therapy device is provided, comprising a conduit structure comprising an upper surface, a lower surface, and a passageway therebetween, a support structure located in the passageway, an inlet opening located in the lower surface, an outlet opening located in the upper surface, a port coupled to the upper surface and in fluid communication with the outlet opening, and a first porous tissue protection structure attached to the lower surface of the conduit structure. The reduced pressure therapy device may further comprise an adhesive structure coupled to at least one of the lower surface of the conduit structure and the first tissue protection structure, and a release liner adhered to the adhesive structure, the release liner comprising a release surface in contact with the adhesive structure, and a second porous tissue protection structure on a surface opposite of the release surface. The release liner may comprise an extension located beyond an edge of the adhesive structure. The first porous tissue protection structure may comprise a different material than the second porous tissue protection structure. The first porous tissue protection device may comprise a foam. The second porous tissue protection device may comprise a woven material. The support structure may comprise a foam. The adhesive structure may be attached to the first porous tissue protection structure. The conduit structure may further comprise a proximal region and a distal region. The inlet opening may be located about the distal region. The outlet opening may be located about the proximal region. The outlet opening may be located halfway between the proximal region and the distal region. The upper surface and the lower surface may be integrally formed. The upper surface and the lower surface may form a seam along an outer perimeter of the conduit structure. The upper surface may comprise a non-planar, vacuum formed polymeric structure and the lower surface comprises a planar polymeric structure. The reduced pressure therapy device may further comprise a dressing attached to the conduit about the inlet opening. An edge of the dressing may be aligned with an edge of the first porous tissue protection structure. The dressing may not overlap with the first porous tissue protection structure. The first tissue protection structure comprises a lateral perimeter portion that extends beyond a lateral perimeter of the conduit structure.

In another embodiment, a bridging device is provided, comprising a flat conduit with a passageway containing a foam structure, a port adhered to a proximal, upper surface of the flat conduit and in fluid communication with the passageway of the flat conduit, a dressing attached to a distal, lower surface of the flat conduit and in fluid communication with the passageway of the flat conduit, and a foam pad attached to a middle and a proximal lower surface of the flat conduit, the foam pad comprising a distal end and an enlarged proximal end, wherein the proximal end comprises a greater width than the distal end. The bridging device may further comprise an adhesive attached to the enlarged proximal end of the foam pad, and a release liner releasably adhered to the adhesive, the release liner comprising a tab extending beyond a perimeter of the adhesive, a fiber material, and a coating on the fiber material that may be releasably adhered to the adhesive. The bridging may further comprise a first end of a tubing coupled to the port, and may further comprise a suction source coupling device attached to a second end of the tubing.

In another embodiment, a method for treating a patient is provided, comprising orienting a dressing with a pre-attached bridging conduit about a tissue treatment site, applying the dressing to a tissue treatment site, and positioning a first skin protection structure attached to an external surface of the bridging conduit in contact with a patient without adhering the first skin protection structure to the patient, wherein a second porous skin protection structure may be releasably preattached to the bridging device. The method may further comprise pulling a porous second skin protection structure preattached to the bridging device, to expose an adhesive, and applying the adhesive to the patient to secure the bridging device to the patient. The method may further comprise attaching a lower surface opening of a second bridging conduit to an upper surface opening of the pre-attached bridging conduit.

In another embodiment, a tissue treatment device is provided, comprising an elongate body with an enlarged proximal end and a distal end smaller than the proximal end, and a cavity therebetween, an elongate support structure located in the cavity and configured to facilitate transmission of reduced pressure along the elongate body, a tubing connector attached to the enlarged proximal end of the elongate body and in communication with a proximal opening of the elongate body, and a wound cover attached to the distal end of the elongate body and in communication with a distal opening of the elongate body, the wound cover comprising a non-rectangular, non-square, non-circular, non-oval shape. The distal opening of the elongate body may have a surface are of at least 1 square cm and through which at least 1 square cm surface area of the elongate support structure is exposed. The wound cover may have a bi-lobed configuration. The wound cover may comprise an open proximal end and a closed distal end. The wound cover may further comprise a tab extending proximally from an edge of the open proximal end. The wound cover may further comprise cavity with a longitudinal axis between the open proximal end and the closed distal end, the cavity comprising a diameter transverse to the longitudinal axis that is less than 4 cm. The diameter transverse to the longitudinal axis may be less than 3 cm or 2.5 cm. The elongate support structure comprises a open-cell foam. The elongate support structure may protrude through the distal opening.

In another embodiment, a method of tissue treatment is provided, comprising attaching at least one wound cover to a treatment site, wherein a foam-based conduit with a tubing connector may be pre-coupled to the at least one wound cover, externally compressing the foam-based conduit, attaching a vacuum source to the foam-based conduit, and activating the vacuum source after externally compressing the foam-based conduit. The method may further comprise maintaining at least some external compression of the foam-based conduit while activating the vacuum source.

Other features and advantages should be apparent from the following description of various embodiments, which illustrate, by way of example, the principles of the invention.

BRIEF DESCRIPTION OF THE DRAWINGS

The features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2A and 2B show side and top cut-away views, respectively, of an embodiment of the device;

FIGS. 7A and 7B show a cross-sectional schematic views of embodiments of a device;

FIG. 8 shows a bottom view of the device from FIG. 1;

FIG. 13A is a superior perspective view of another bridge device.

FIG. 13D is an inferior perspective view of the bridge device of FIG. 13A attached to a port, tubing and tubing connector;

FIGS. 17A and 17B are perspective superior and inferior views of another variant of a digit device;

FIG. 19 is a superior elevational view of another variation of a branching device.

DETAILED DESCRIPTION

Figure 1:
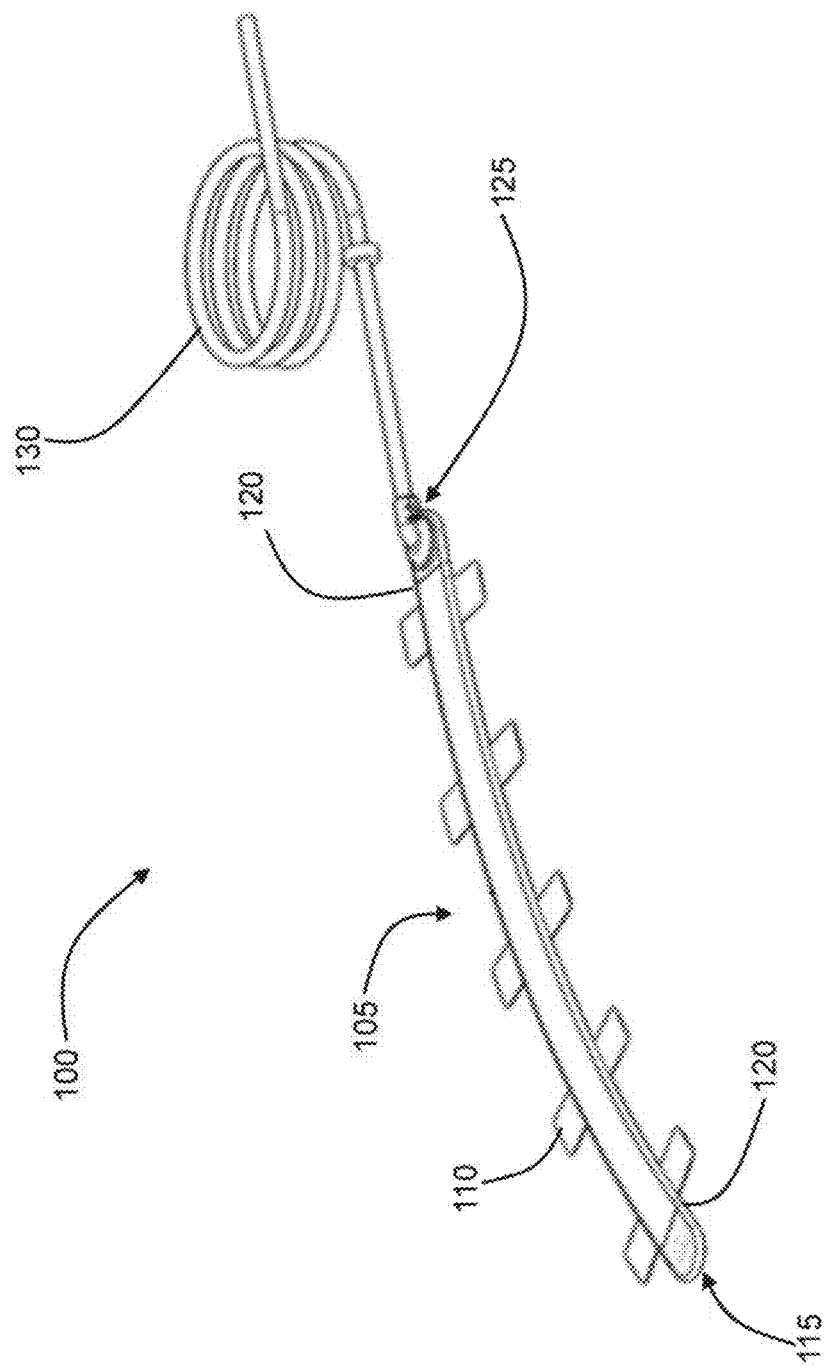
FIG. 1 shows a perspective view of an embodiment of the device for use with a negative pressure dressing system.

Diabetic patients also often experience chronic ulcers of the lower extremity. Often, these ulcers are located on the plantar region of the foot, typically near the heel or metatarsal head. Some anatomical regions have contours or geometries that make application of a dressing somewhat challenging, especially in the case of RPWT where a seal between the skin and dressing is used to generate therapeutic vacuum at the wound site. Some anatomical regions such as the sacrum and the plantar region of the foot are subject to certain contact forces on the dressing and/or wound surface such that the dressing itself can worsen the condition of the wound being treated or cause damage to neighboring tissues. In some cases, the contact forces are unavoidable and in others are due to patient non-compliance or in the case of neuropathy a patient may be unaware that they are loading their wound location.

In the case of RPWT, components of the device can contribute to limiting or preventing wound healing, creating additional wounds or even worsening the condition of the wound being treated. Furthermore, maintenance of a sufficiently airtight seal between a dressing and an anatomical region subject to contact forces may be compromised reducing the ability of the dressing to draw exudates away from the wound. For example, mechanical deformation caused by patient movement, accumulation of moisture (e.g., sweat or interstitial fluid), and by the reduced pressure itself can each affect the seal of the dressing and ability of the dressing to draw away fluid.

However, by providing a bridging conduit as described herein, between the wound dressing and the vacuum source, some components of a reduced pressure wound treatment device, such as a port connector that would otherwise protrude from the outer surface of a wound dressing, the port connector may be moved to a location remote to the wound dressing, where the mechanical consequences of the port connector may be less concerning.

The devices and systems described herein can deliver negative pressure to a wound and reduce pressure points in various anatomic regions, including but not limited to the sacral region, foot (including the heel, plantar surface and dorsal surface), elbow, digits (including fingers and toes), amputation stumps, skin flaps, skin grafts and other contoured body parts, and maintain an adequately airtight seal in any position (e.g., sitting, standing, lying, etc.) or movement (e.g., walking, rolling, bending, etc.). The devices and systems described herein have a low profile and low peak pressure interface with the sealing layer and can reduce the potential for additional tissue damage or healing impairment from excessive pressure applied to the wound site or surrounding tissues. The devices herein may also reduce shear forces acting at the dressing-skin interface, which may cause separation or lifting of the dressing, thereby compromising the seal interface and therapeutic negative pressure delivery.

The device is described herein in the context of the tissue being skin, although it should be appreciated that the device can be used with biological tissue other than skin. Further, it should be appreciated that the devices described herein can be used with a variety of wound dressings used to deliver negative or reduced pressure. Generally, use of the terms "reduced" or "negative" pressure refers to a pressure that is less than the ambient pressure at a particular tissue site that is being subjected to the treatment. The magnitude of the pressure reduction may be characterized as a negative value relative to ambient pressure (e.g. −50 mm Hg, −75 mm Hg, −100 mm Hg and −125 mm Hg), or the degree of the pressure reduction may be characterized by the absolute pressure level (e.g. a pressure level between an absolute vacuum of 0 mm Hg and 760 mm Hg atmospheric pressure). Use of the term "wound" should not be limited to any particular type of injury, discontinuity or disorder of the skin and underlying tissue layers. The wound can include a chronic open wound such as a diabetic foot ulcer or decubitus pressure sores, venous stasis ulcers, or traumatic or surgical wounds or incisions that are open like burn injuries or have been closed with sutures, staples, adhesives and the like.

Now with respect to FIG. 1, the device 100 may include a flexible, low-profile, conduit body 105, one or more adhesive tabs 110, a distal port 115, and a proximal port 125. The distal port 115 may connect to a wound dressing positioned at a wound site. The proximal port 125 can connect, for example via tubing 130, to any of a variety of negative pressure sources (not shown). The device 100 may be configured to create and maintain a fluidic pathway or channel for the delivery of negative pressure to and removal of exudates from the wound site while preventing collapse of the system when external forces are applied. The device 100 may perform these functions while avoiding or reducing further exacerbation of a wound site due to pressure points. Also, relative movement between the conduit body 105 and the underlying skin surface is prevented thereby avoiding rubbing or the creation of new skin trauma due to the device itself.

The wound dressing can vary and can include the devices and dressings described in co-pending U.S. Pat. Publ. No.

2010/0174250, filed Jan. 7, 2010, which is hereby incorporated by reference in its entirety. Similarly, the negative pressure source can vary, including an electric vacuum pump, in-wall suction, or a non-electrically powered suction device. Components and devices that can be used to provide reduced pressure therapy at a wound site have been described in co-pending U.S. Pat. Pub. No. 2010/0137775, filed on Nov. 25, 2009, which is hereby incorporated by reference in its entirety.

The device 100 may be used to bridge between a dressing at a wound site and a remote location such as a non-wound region of healthy skin or a non-load bearing location. The device 100 can also be used to bridge between two or more wound sites. The dimensions of the conduit body 105 can vary. The conduit body 105 may have various lengths and the distance between the distal port 115 and the proximal port 125 can vary. In one embodiment, the conduit body 105 is in the range of about 16 inches to about 26 inches or more, or more particularly about 18 inches to about 24 inches, such as for use with a sacral wound. In another embodiment, the conduit body 105 may have a length in the range of about 2 inches, about 4 inches, about 5 inches, about 7 inches, about 8 inches, about 9 inches, about 10 inches, about 11 inches or about 12 inches such as for use with a foot wound. The conduit body 105 may also have a configuration such that the length that can be resized or customized to a length suitable for a particular patient or wound location. The proximal port 125 may also be configured to be resized or customized to a length suitable for a particular patient or wound location. As an example, the proximal port 125 may include a connector that can directly interface with the reduced pressure source or can connect to tubing 130, which then interfaces with the reduced pressure source. The proximal port 125 may be configured to attach to the conduit body 105 or can be configured such that the conduit body 105 may be shortened and the proximal port 125 plugs into or otherwise sealably couples to the open, shortened end. For example, the conduit body 105 may be cut to a desired length and accept a barbed connector in the open, cut end. It should be appreciated that the distal port 115 may connect to a location other than the wound dressing. For example, the distal port 115 can connect to a proximal port 125 of another device 100 to serially connect multiple devices 100, of the same or different configuration.

Figure 3:
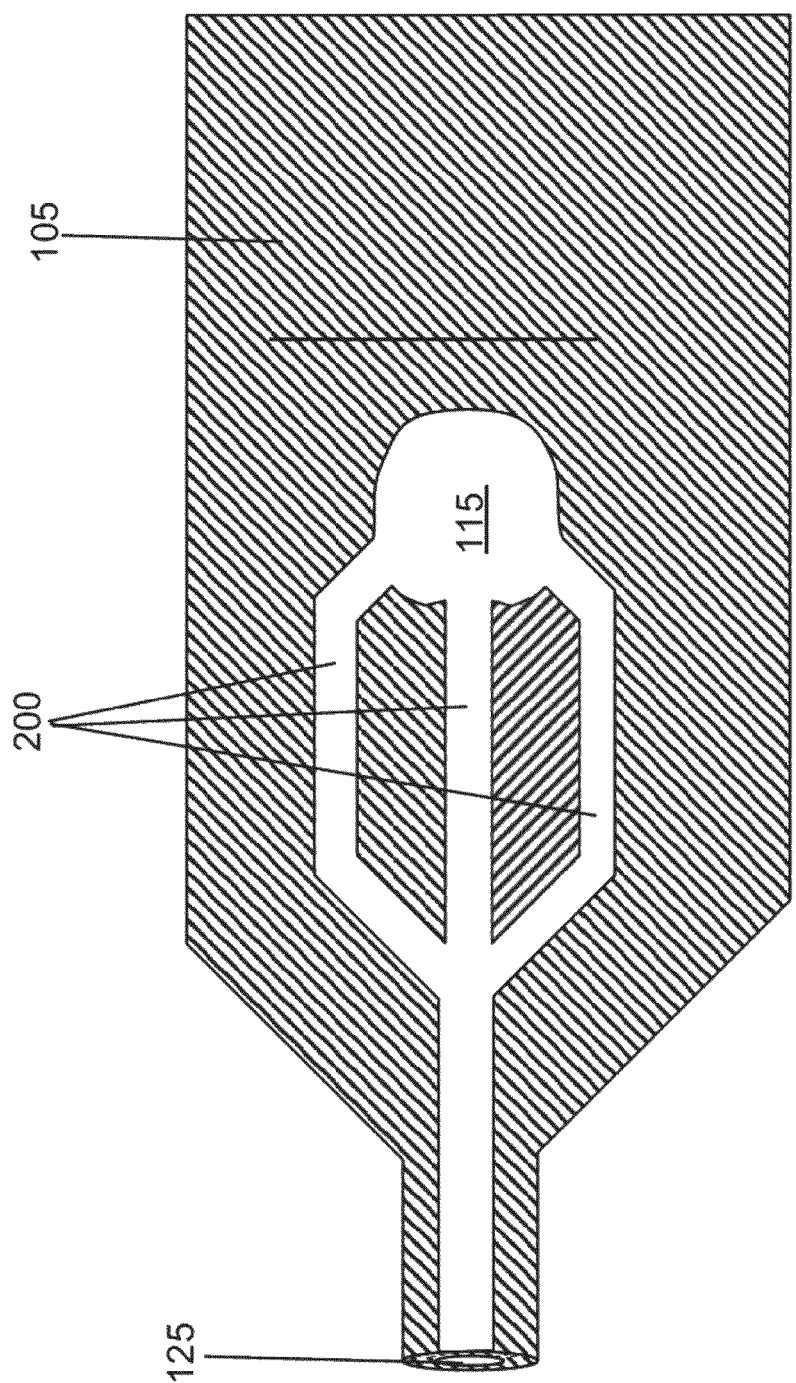
FIG. 3 shows a top, cut-away view of another embodiment of the device.

As best shown in FIGS. 2A and 2B, a channel 200 can extend through the conduit body 105 from the distal port 115 to the proximal port 125. It should be appreciated that more than a single channel 200 can extend through the conduit body 105 to the proximal port 125 as shown in FIG. 3. Multiple fluidic channels 200 can minimize opportunities for complete occlusion of the conduit body 105 to occur.

Figure 4:
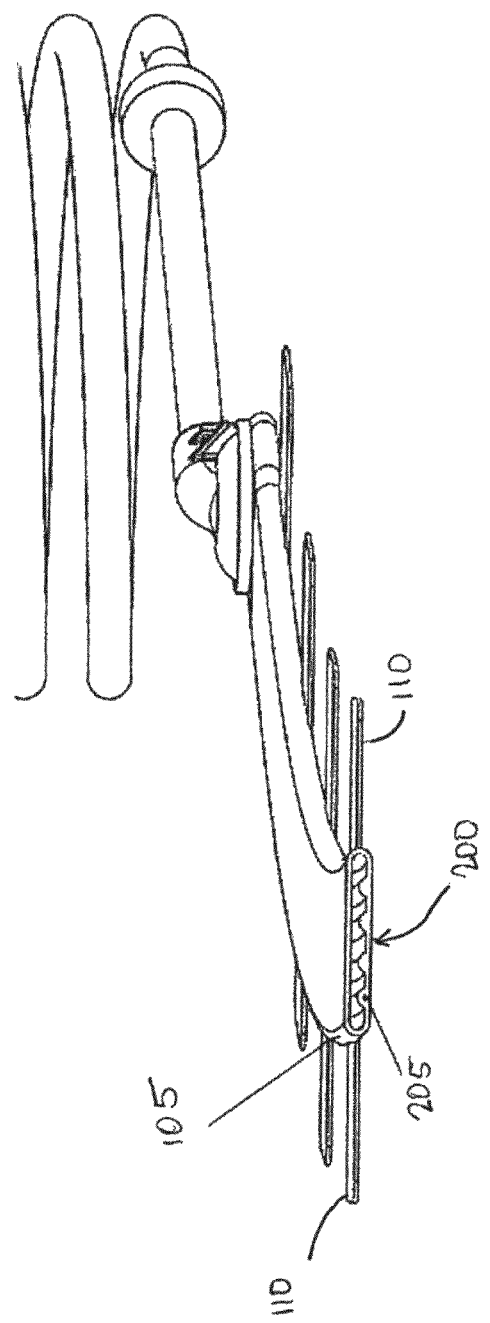
FIG. 4 shows a cross-sectional view of the conduit portion of the device from FIG. 1.

FIG. 4 shows a cross-sectional view of the conduit body 105 having a central channel 200 running through it. The conduit body 105 can have a cross-section that is generally low profile and non-circular. The cross-sectional shape of the conduit body 105 in FIG. 4 is oval, but it should be appreciated that the shape can vary including, but not limited to, generally flattened, planar, elliptical, rectangular, or other shape, for example to provide the conduit body 105 with the flexibility to hug a curve of an anatomical structure such as a foot. The geometry of the conduit body 105 can be configured such that the elongated side of the conduit body 105 is positioned and/or adhered relatively flush with the skin surface and allows for better deformation of the device 100 when external forces are applied to the conduit body 105. The cross-sectional shape of the conduit body 105 can help to mitigate conduit collapse and also prevent or dissipate pressure points. The conduit body 105 can have a width to height ratio that can vary depending on where the conduit body 105 is to be located. For example, the conduit body may be between 4 to 6 inches wide for a sacral application, whereas the conduit body 105 may be narrower for use with the foot, such as ½ to 2 inches wide. In some embodiments, the conduit body 105 may be approximately 1 to 2 inches wide and $\frac{1}{16}$ and $\frac{1}{4}$ inch tall, but it should be appreciated that these dimensions can vary. Generally, the conduit body may comprise a width that is larger than the height.

The material of the conduit body 105 can vary, including, but not limited to polyolefins, polypropylene, polyethylene, polyesters, polyethylene terephthalate, polyamides, nylon, silicone, and polyurethane. Generally, the material of the conduit body 105 can be non-irritating and biocompatible. The materials can be opaque, translucent or transparent. The materials may possess uniform or variable mechanical properties and geometries to maintain channel patency while allowing for conformability and flexibility. The material durometer may range from 20 to 70 on a Shore A hardness scale and materials of different durometers may be combined to achieve desired operating characteristics.

The conduit body 105 can also include one or more support structures 205 protruding into the channel 200. The support structures 205 prevent or mitigate collapse of the channel 200 upon application of internal vacuum, external pressure to or compression of the conduit body 105, which may provide some residual fluid flow. This may prevent or reduce the risk of interruptions of negative pressure therapy to the wound site due to blockage. The support structures 205 may also prevent or reduce significant pressure concentration during load-bearing.

Figure 5:
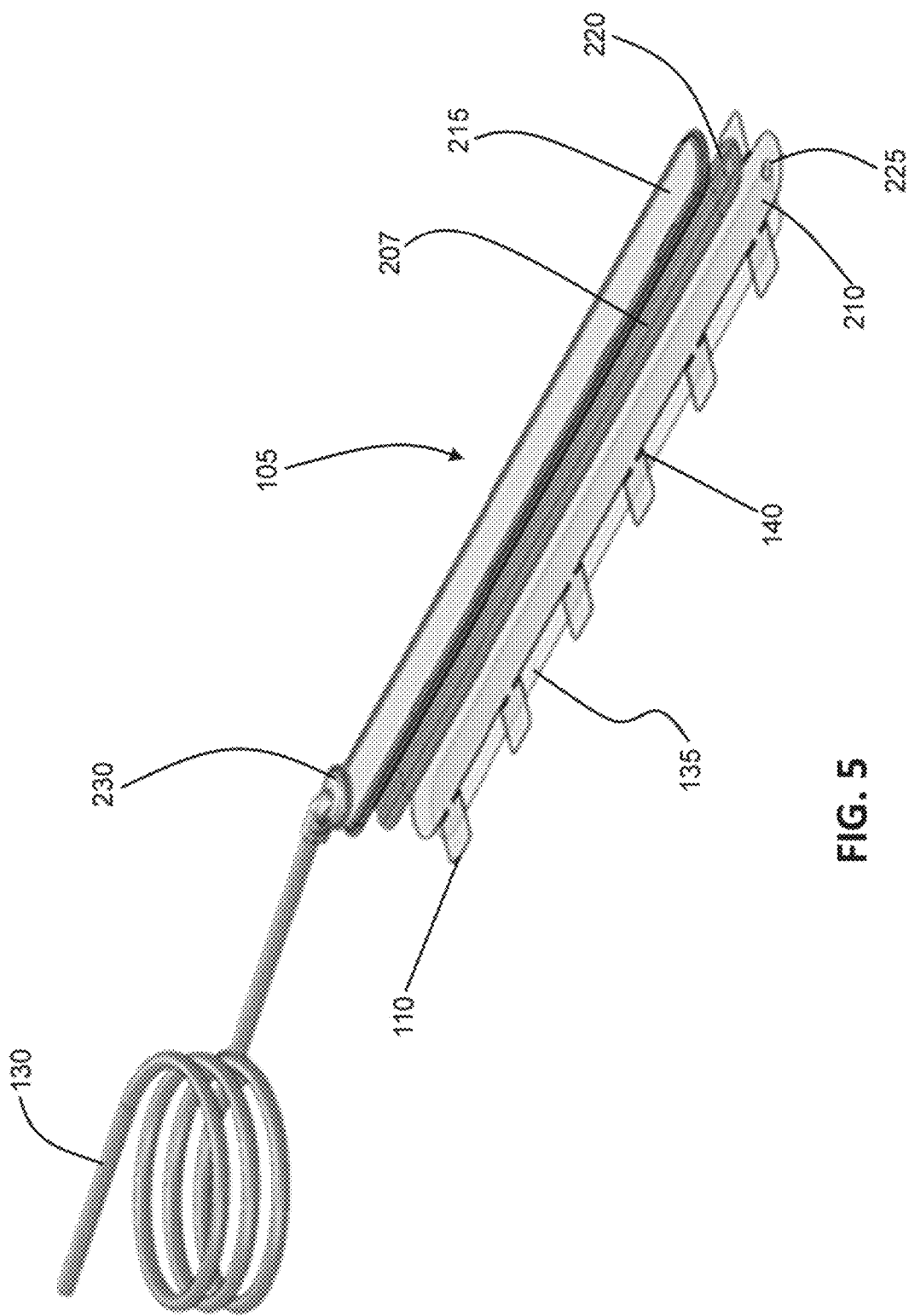
FIG. 5 shows an exploded view of an embodiment of the device.
Figure 6:
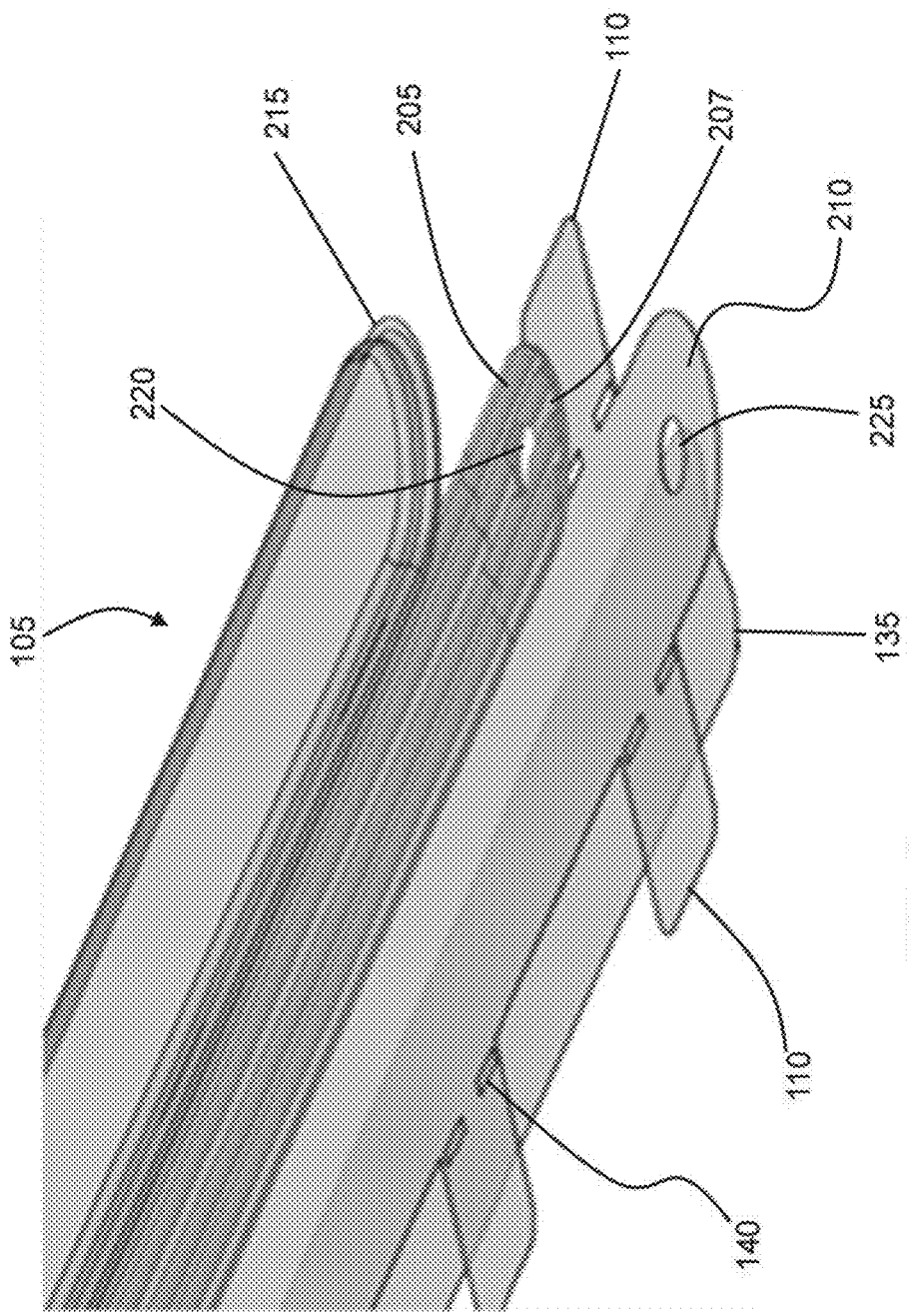
FIG. 6 shows a close-up of the exploded view of the device of FIG. 5.

The configuration of the support structures 205 can vary. For example, FIG. 4 shows the conduit body 105 as a single component having a plurality of support structures 205, such as one or more elongate ribs or other three-dimensional features, coupled to an inner wall of the conduit body 105. The support structures 205 may be integrated together with the walls of the conduit body 105, the support structure 205 and the conduit body 105 may be molded or extruded in an integral fashion. In other examples, however, the support structures 205 need not be integrated with the walls of the conduit body 105. Instead, the conduit body 105 can have a multi-layer or multi-component construction as shown in FIGS. 5 and 6, where two or more components may be bonded together, for example, by heat welding/radio frequency (RF) welding process, adhesives, or other bonding processes. The support structures 205 can be three-dimensional elements that protrude from an upper surface of a generally planar, middle layer 207 that is sandwiched between an upper cover 215 and a lower base 210. The support structures 205 of the middle layer 207 can provide support to the upper cover 215 such that upon exertion of an external force complete collapse of the channel 200 is prevented or reduced. The support structures 205 can also include one or more individual elements positioned within at least a portion of the channel 200 between the cover 215 and base 210 (see FIGS. 7A and 7B). The support structures 205 can be positioned within a central portion of the channel 200, near a side portion of the channel 200, or a combination of the two. The support structures 205 can be punctile structures, elongate ribs, corrugations, or form a criss-cross or egg-crate pattern. The support structures 205 can have a rounded, semi-spherical, square, polygonal, or other cross-sectional shape. The support structure 205 can also include a mesh-like structure such as a synthetic textile structure with sufficient porosity to allow the delivery of reduced pressure and flow of fluid. The support structure 205 may comprise any of a variety of resilient porous structures or materials, including but not limited to foam, woven or non-woven spacer fabrics. The support structure 205 can include a fabric or other material having open channels running therethrough. Where the support structure comprises a porous material, such as a foam or a fabric-like material, the structure may comprise a block or layer-like structure, or may also comprise the configurations recited above, e.g. corrugations or egg-crate pattern.

In some embodiments, the support structures 205 may be manufactured from a pliable polymeric material such as silicone or urethane or a material such as cotton or gauze or other readily formed material having a configuration so as to maintain the flow channel 200 when load-bearing over the conduit body 105. The material can be compliant such that it maintains its own structure when a force is applied and then removed. The material can, but does not necessarily have memory. Generally, the material of the support structures 205 has a low durometer such that it can allow for greater deformation of the conduit body 105 when external forces are applied in order to more evenly distribute those forces such as when a patient with a wound on the plantar surface of the foot walks or a patient with a wound on or near the sacrum lies down. In an embodiment, the durometer of the material is less than 65 Shore A. In another embodiment, the material is less than about 50 Shore A, 40 Shore A, 30 Shore A, or 20 Shore A. The material used for the support structure 205 can be the same or different from the material used for the conduit body 105. In an embodiment, the material used for the support structure 205 may be generally stiffer and has a higher durometer than the material used for the conduit body 105. In another embodiment, the material used for the conduit body 105 is generally stiffer and has a higher durometer than the material used for the support structure 205. In another embodiment, the material used for the conduit body 105 and the support structure 205 have generally the same stiffness and durometer. In this embodiment, one structure can have a geometric difference that affects a more sturdy aspect to prevent or resist collapse.

A lower surface or "wound side" of the conduit body 105 may provide fluid communication between a wound dressing and the channel 200 of the conduit body 105 with the negative pressure source via the distal port 115. In an embodiment shown in FIGS. 5 and 6, the lower base 210 and the support structure layer 205 can each include distal apertures 220, 225 that align to create the distal port 115 of the conduit body 105. Exudate may flow from the wound site through the apertures 220, 225 and into the channel 200 created between the support structure 205 and the upper cover 215.

As best shown in FIG. 8, the lower surface of the conduit body 105 at or near the distal port 115 may include or be at least partially covered by an adhesive 145 for connection to a wound dressing. The adhesive 145 can surround at least a portion of the opening to the distal port 115. The adhesive 145 may or may not sealably adhere the conduit body and the wound dressing together. In some further variations, a separate or additional grommet may be provided to couple the conduit body and the wound dressing via their fluid communication openings. It should be appreciated that the distal port 115 can connect to a wound dressing using other mechanisms such as a static seal or a suction cup seal.

Figure 9:
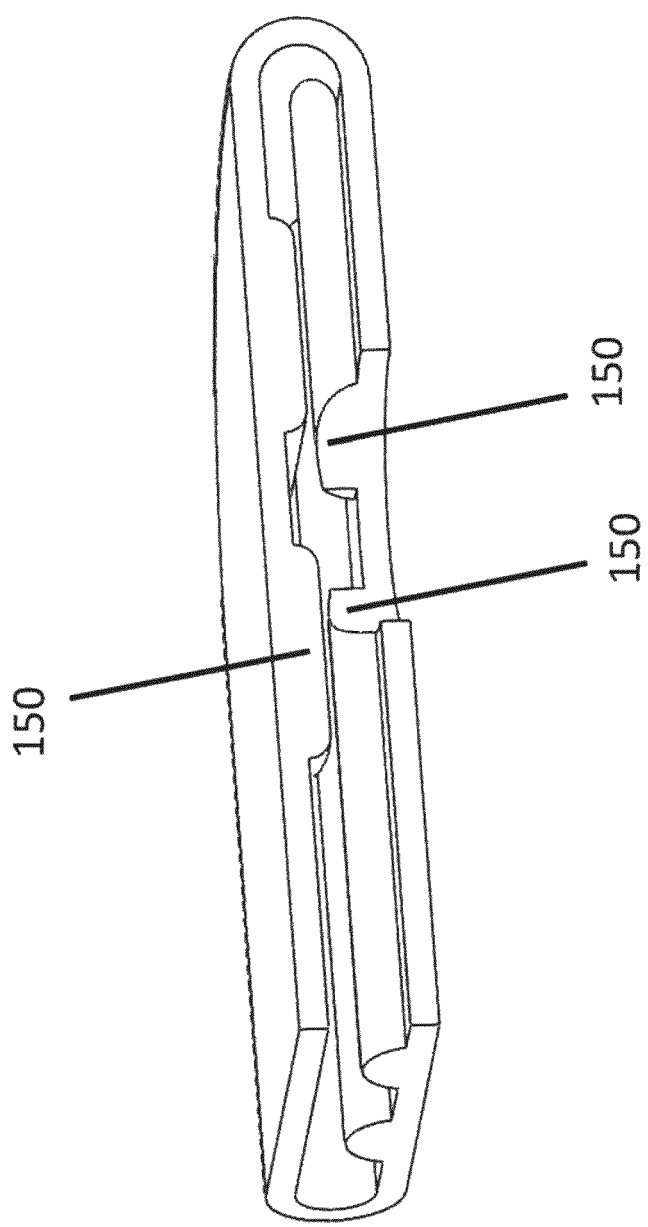
FIG. 9 shows a cut-away side view of a portion of the device.

The distal port 115 may be configured to resist closure upon application of a load, but is still soft enough to mitigate formation of pressure points. The distal port 115 may be used at the wound surface and can have a construction that disperses pressure points while maintaining fluidic pathways within the port to allow for the delivery of negative pressure and removal of exudates. An interior region of the distal port 115 may include one or more supports 150. The supports 150 also may prevent or resist the channel 200 from collapsing around the opening of the distal port 115. FIG. 9 is a cut-away side view of the device near the opening of the distal port 115 showing a configuration of supports 150 surrounding the opening of the port 115. The supports 150 may be arranged such that the opening of the port 115 is maintained even when external pressure is applied to the port 115. The supports 150 may evenly distribute loads applied to the distal port 115 and mitigate pressure points by virtue of their generally flat shape with minimal protrusions. The distal port 115 can have a broad configuration such that forces on the distal port 115 tend not to create pressure points underneath. The distal port 115 can have a wide skirt such that when a patient applies a force to the site the pressure is not concentrated at a singular point. The skirt may also be tapered to reduce pressure concentration at the edges of the distal port 115.

As mentioned above, one or more adhesive tabs 110 can be used to secure the device 100 to the patient's body. The tabs 110 may extend outward on opposite sides of the conduit body 105. Alternatively, each tab 110 may extend from the conduit body in an alternating or offset fashion on each side of the device, rather than in pairs as shown in FIG. 5. The device 100 may also be secured to the patient's body using a continuous sheet of material as opposed to individual tabs. The tabs 110 may be formed of a breathable material, such as polyurethane or silicone, that is coated on a lower, skin-facing surface with a skin-friendly adhesive. Skin-friendly adhesives can include acrylics, hydrocolloids or silicone adhesives, for example, that may be configured to absorb or transport moisture from the skin and generally maintain skin health. As best shown in FIGS. 5 and 6, the tabs 110 may include perforations 140 near where the tabs 110 extend or protrude outward from the conduit body 105. The perforations 140 allow for the tabs 110 to be easily removed if deemed unnecessary or undesired for the application of the device 100 to the patient. The adhesive tabs 110 can be covered by one or more paper or polymeric backing layers (not shown) such that the device can be secured to a patient's body in an easy and controlled manner.

As noted above, in some embodiments, the support material or structure in the device may comprise a resilient, compressible material such as a mesh structure, a synthetic textile, foam, cotton, gauze, and the like. In some variations, while the support material may be generally soft and conformable at atmospheric pressure, when subjected to negative pressure, the material may become substantially compressed and possibly more rigid or hard. In some variations, for example, a more rigid or hardened foam structure may generate relatively more skin or tissue pressure points or regions, in comparison to the non-evacuated foam structure. For these and other reasons, it may be beneficial to provide a skin protective pad or material on the underside of the device configured to contact the skin.

The device 100, for example, may also include an underlying contact surface 135 (see FIGS. 5 and 6) positioned in direct contact with the skin under the device 100. The contact surface 135 can also be integrated with the device 100. The contact surface 135 may comprise a material such as a natural breathable material like cotton gauze to maintain dryness of the underlying skin and that has natural evaporative or liquid wicking properties, such as rayon. The contact surface 135 may be generally thin and can be transparent. Alternatively, the contact surface 135 can be a compliant material, such as a porous foam or a woven or non-woven textile that is skin-friendly as described above, and that can provide cushioning for further comfort to a patient wearing the device 100. It should be appreciated that the contact surface 135 can be a variety of materials including, but not limited to polymeric material such as polyurethane, elastomeric polyester, or polyethylene, foam, mesh, gauze, sponge, stacked mesh matrix, adhesive, hydrocolloid, hydrogel, acrylic adhesive or other biocompatible material. The contact surface 135 may be adhesively coated in some embodiments. The adhesive coating may be located contiguously or non-contiguously along the perimeter or spaced apart regions along the contact surface 135.

Referring back to FIG. 1 the conduit body 105 may have two connection junctions 120 along its length such that the conduit body 105 includes three separate parts that can be joined together during manufacturing. Alternatively, FIGS. 5 and 6 show the conduit body 105 having a multi-layer or multi-component construction. The layers of the conduit body 105 can be heat bonded, ultrasonic, friction bonded, RF or laser welded or otherwise adhered together.

One or both of the ports 115, 125 can include a pressure sensitive mechanism or indicator 230 (FIG. 5) that provides information to a user about the pressure being delivered through the conduit body 105 and locally to the wound site. The indicator can include those embodiments described in U.S. Publ. No. 2010/00137775, filed on Nov. 25, 2009, which is hereby incorporated by reference in its entirety. The indicator 230 can provide assurance to a user that the desired reduced pressure level is delivered to the wound for optimal therapy and the pressure is not occluded or otherwise not compromised such as by clogging of the fluid communication conduit between the reduced pressure source and the dressing on the wound site. The indicator 230 can be positioned in one or more locations along the device 100 such as within the tubing 130, on a region of the conduit body 105, near the distal port 115 or proximal port 125. In an embodiment, the indicator 230 can be integrated into the body of the distal and/or proximal ports. The indicator 230 can be a radial section of a compliant material that surrounds a region of the port or forms an exterior wall of the port covering an interior wall and/or at least a portion of the wound site. A volume between the compliant exterior wall and the wound site can be reduced and the compliant exterior wall deformed upon exposure of the volume to reduced pressure or formation of a pressure gradient upon delivery of reduced pressure to the wound site by a reduced pressure source. The indicator 230 can provide an indication of the pressure under the structure and whether or not the pressure gradient is sufficient or is lost or compromised. The indicator 230 can provide a visible and/or tactile notification to a user regarding the pressure gradient.

The exterior wall of the indicator 230 may be translucent, transparent or opaque. In one embodiment, the exterior wall of the indicator 230 is translucent and obscures a visually distinctive region when the exterior wall is a distance away from the wound site. When a pressure gradient is present the exterior wall of the indicator 230 can approach the wound site and decrease the distance between the exterior wall and the visually distinctive region until the visually distinctive region is visible through the exterior wall. The visually distinctive region can include a color, pigment, symbol, pattern, text and the like. In an embodiment the exterior wall of the indicator 230 can be a first color and an interior wall can be a second color such that contact between the exterior wall and the interior wall provides a visible indication of the pressure gradient due to change in color. Deformation of the exterior wall of the indicator 230 can result in a change from a first profile to a second profile. In an embodiment, the relative position of the exterior wall between the first profile and the second profile can be indicative of an amount of pressure delivered to the wound site. The change in profile can also provide a tactile change.

Figure 10A:
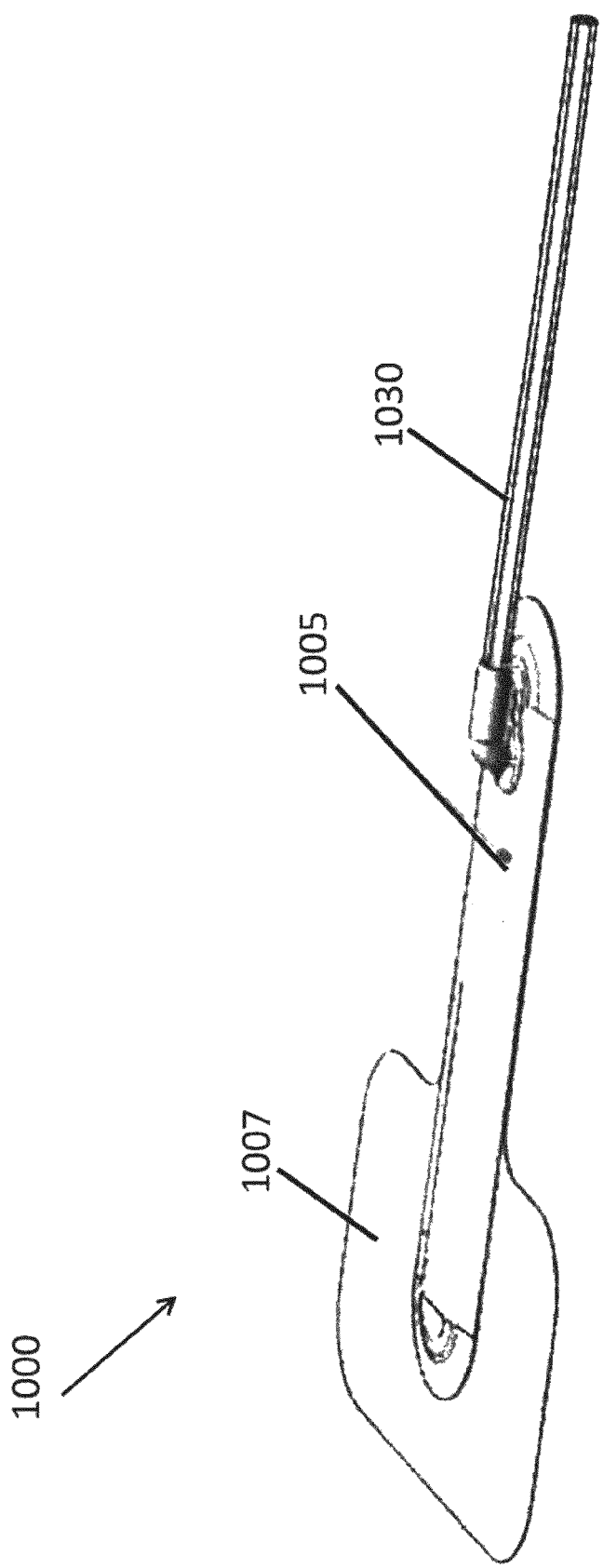
FIG. 10A is a perspective view and FIG. 10B is an exploded view of another embodiment of a device.
Figure 10B:
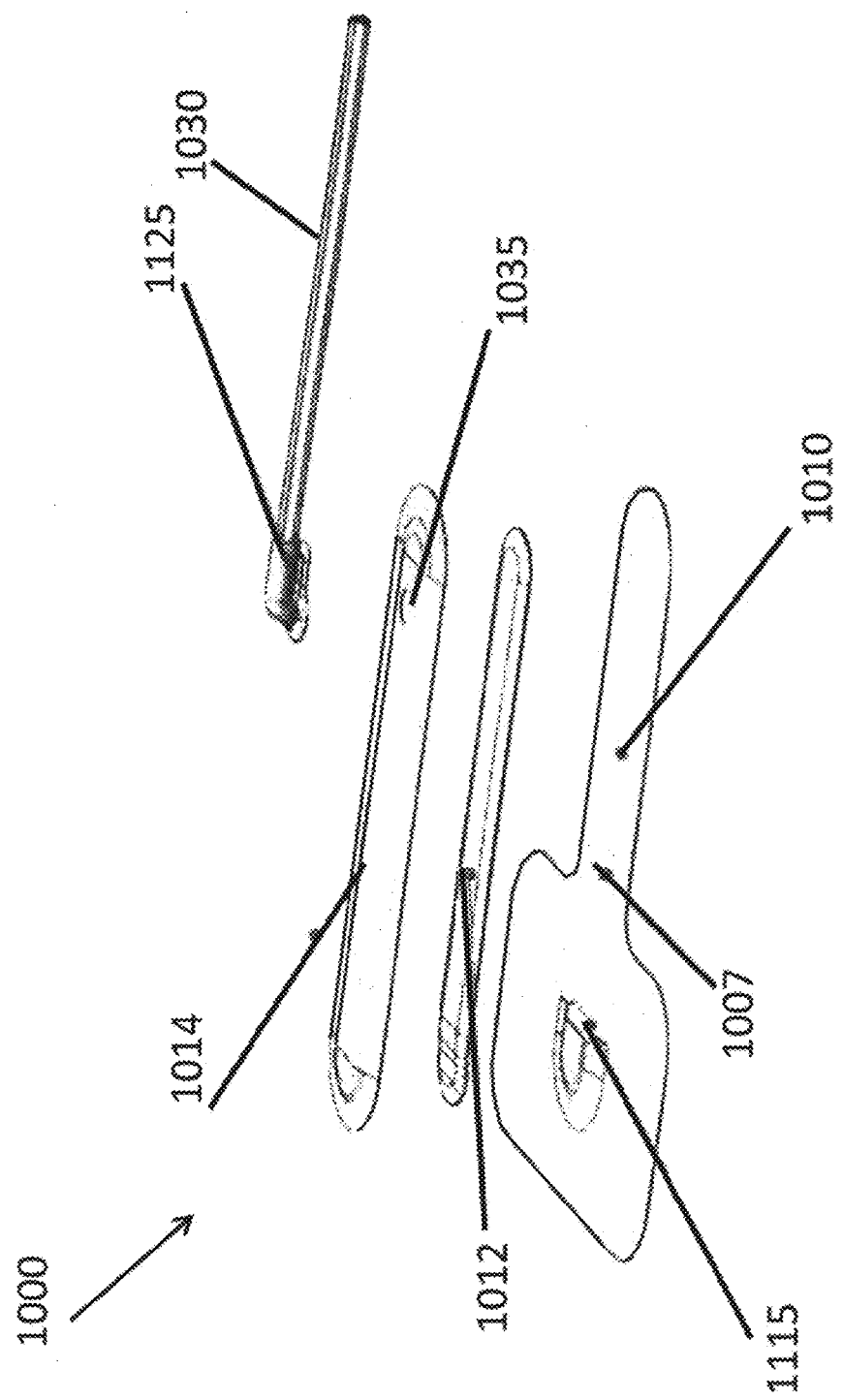

FIGS. 10A and 10B depict another embodiment of a device 1000. The device 1000 may include a flexible, low-profile conduit body 1005 extending from a thin, flexible sealing layer 1007 configured to seal over a wound site. The sealing layer 1007 may have a distal aperture 1115 that aligns with a distal portion of the conduit body 1005 such that reduced pressure can be delivered to the wound site through the conduit body 1005. Reduced pressure can be delivered from a reduced pressure source (not shown) through the conduit body 1005, which can include a proximal aperture 1035 configured to couple to a proximal port 1125 and tubing 1030 extending from the reduced pressure source.

As shown in FIG. 10B, the sealing layer 1007 may include an elongate extension 1010 defining a skin-side portion of the conduit body 1005. The conduit body 1005 may include an inner spacer 1012 and a top layer 1014. The inner spacer 1012 of the conduit body 1005 may be a porous material sealed circumferentially, e.g. by laminating together the edges (or other regions) of the elongate extension 1010 and the top layer 1014. The elongate extension 1010 and the top layer 1014 can each be thin sheets of impermeable material. The inner spacer 1012 may also be sealed circumferentially by one sheet of impermeable material wrapped around it and the two free ends sealed. The inner spacer 1012 of the conduit body 1005 can include foam, fabrics, such as spacer fabric, 3-D knitted or woven fabrics, or one or more molded features as described above that allow the conduit body 1005 to stay patent when a negative pressure is applied or external pressure is exerted against the conduit body 1005.

The sealing layer 1007 can be hydrocolloid or other material such as hydrogel, acrylic, polyurethane, and others. The sealing layer 1007 can include a skin-friendly adhesive to obtain a substantially airtight seal of the wound. The same adhesive can coat both the skin-side portion of the conduit body 1005 and the sealing layer 1007. The sealing layer 1007 can be adhered down to the patient's skin surrounding the wound site. The conduit body 1005 leading from the wound site can also be adhered down to the patient's skin preventing movement of the conduit body 1005 relative to the patient's skin, which can cause shear trauma. The adhesive can be masked off or otherwise interrupted near the junction of the sealing layer 1007 and the conduit body 1005 to stop peel propagation of the conduit adhesive to the sealing layer and potentially disrupt the wound seal. A separate release liner (not shown) can be used on the conduit body 1005 and the sealing layer 1007 to help with the manipulation of the device 1000 during application.

Figure 11A:
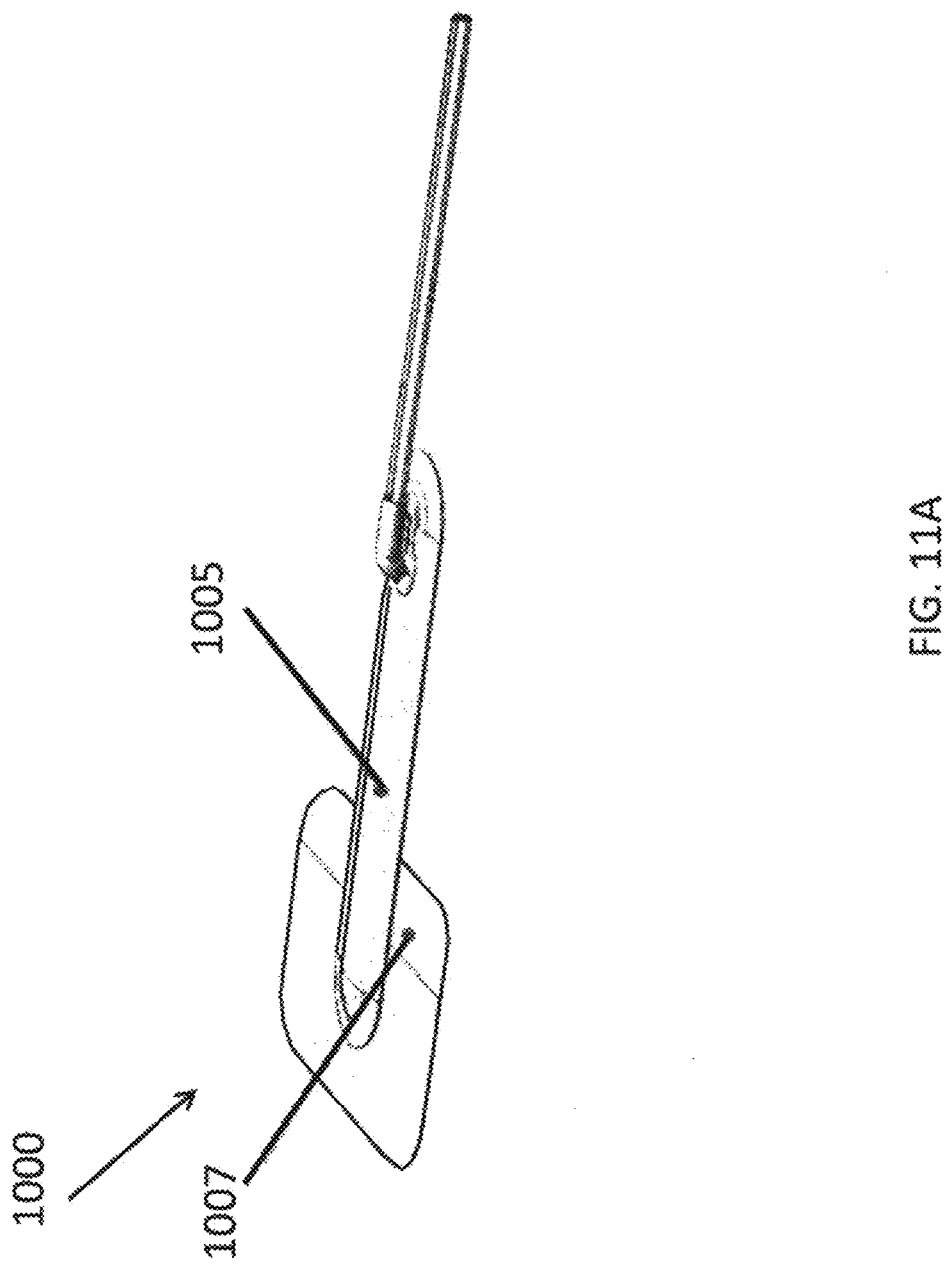
FIG. 11A is a perspective view and FIG. 11B is an exploded view of another embodiment of a device.
Figure 11B:
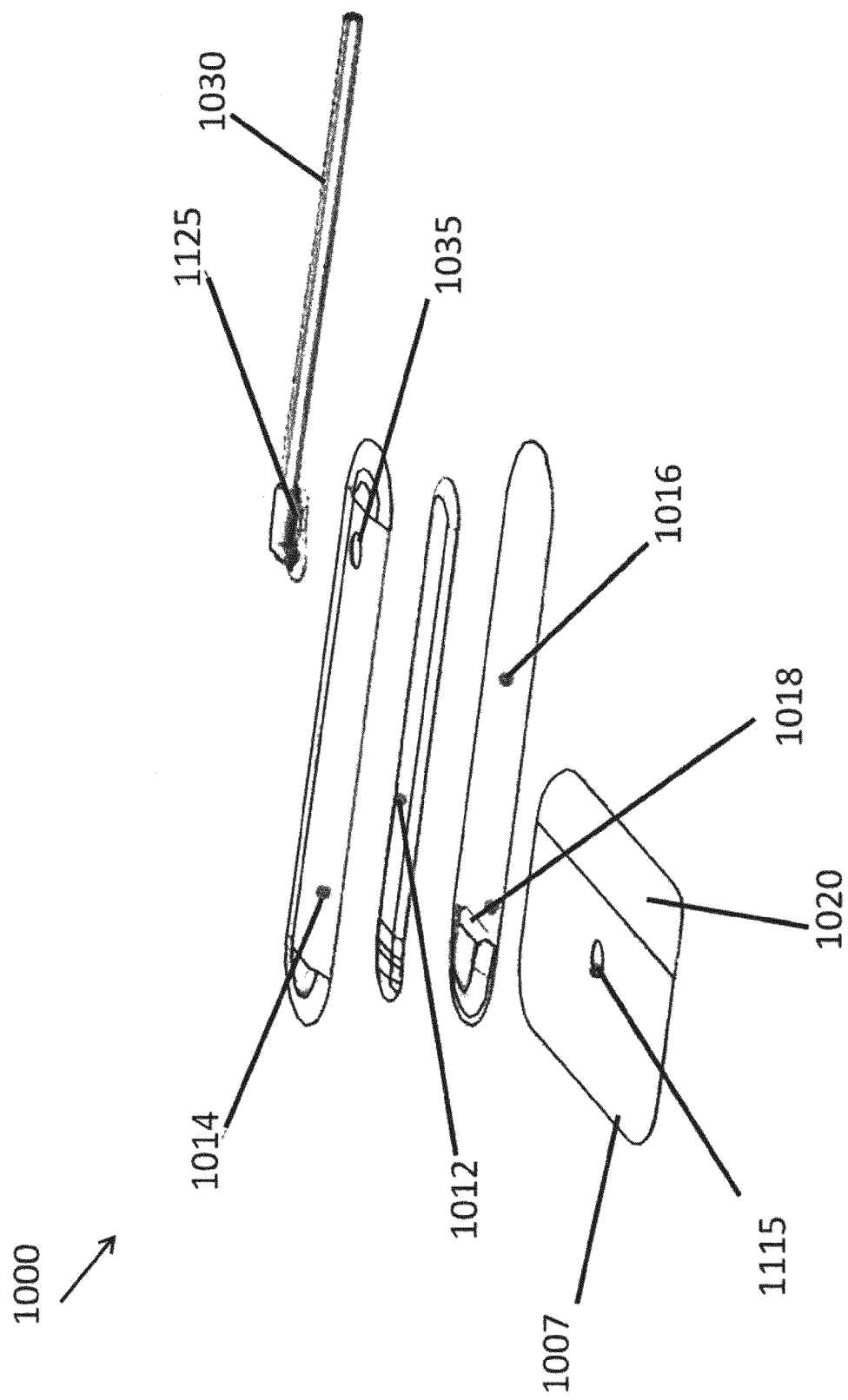

The sealing layer 1007 may or may not include an elongate extension 1010 to which the inner spacer 1012 and top layer 1014 of the conduit body 1005 are attached, as described above. The conduit body 1005 can include an inner spacer 1012 sealed circumferentially by a top layer 1014 and a lower layer 1016 as shown in FIGS. 11A and 11B. The conduit body 1005 can also include an inner spacer 1012 sealed circumferentially by a single sheet of impermeable material. The lower layer 1016 of the conduit body 1005 can be coupled to an upper surface of the sealing layer 1007. In an embodiment, a distal aperture 1018 of the lower layer 1016 of the conduit body 1005 can be generally aligned with or surround the distal aperture 1115 of the sealing layer 1007. The spacer 1012 can pass through the aperture 1018 of the lower layer 1016 such that at the distal end of the conduit the spacer 1012 is positioned below the conduit body 1005. In this example, the aperture 1115 can align with the spacer 1012, but not necessarily align with the aperture 1018 through which the spacer 1012 passed. The lower layer 1016 of the conduit body 1005 can be coupled to the sealing layer 1007 by permanent bonding or by a reversible adhesive.

Figure 12:
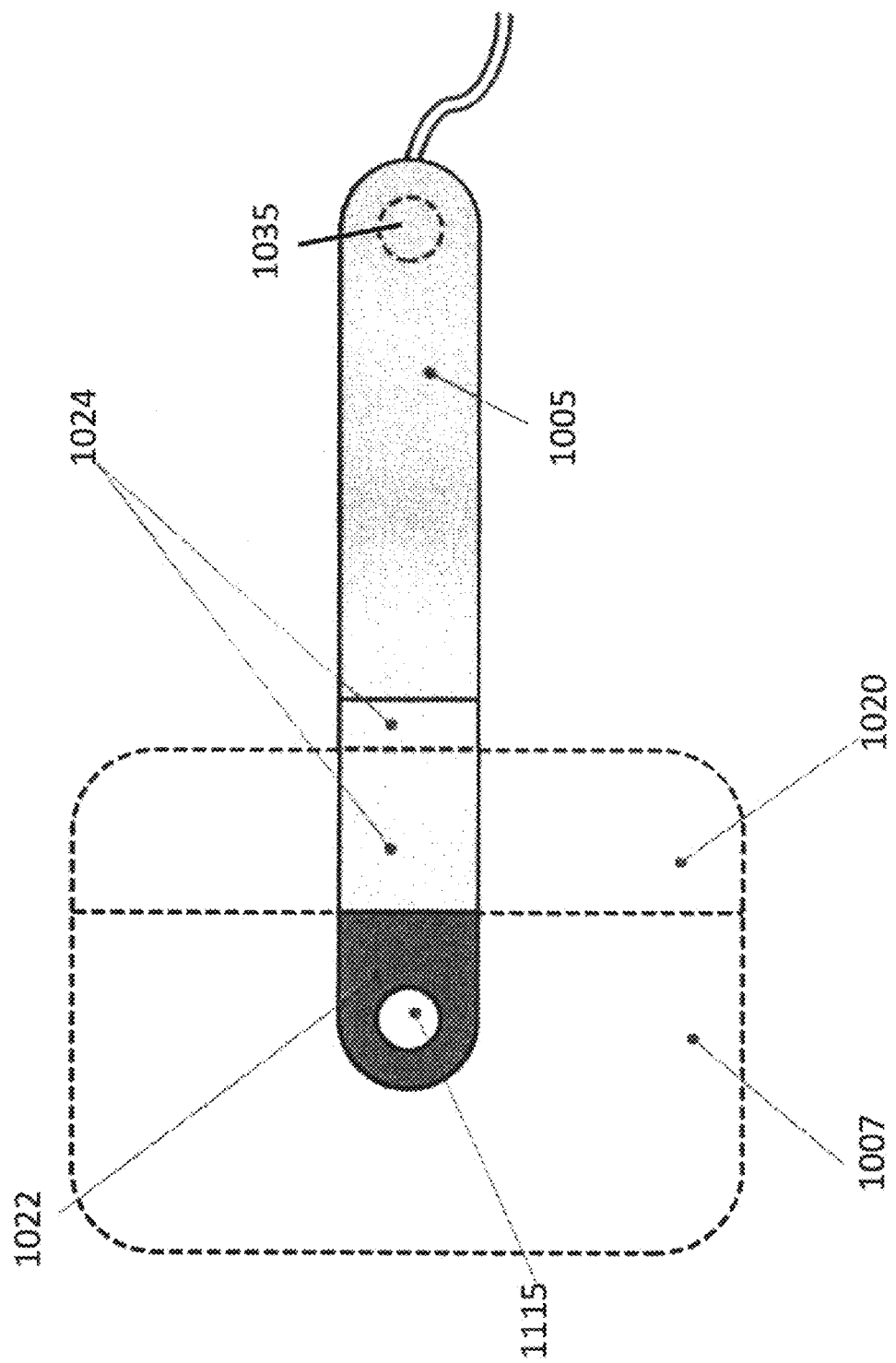
FIG. 12 is a schematic view of an underside of the device of FIGS. 11A-11B.

In an embodiment best shown in FIG. 12, the conduit body 1005 is coupled to the sealing layer 1007 in region 1022 surrounding the distal aperture 1115 of the sealing layer 1007. The conduit body 1005 is not coupled to the sealing layer 1007 in region 1024 near an edge of the sealing layer 1007. This creates a flap 1020 on the sealing layer 1007 that remains free relative to the conduit body 1005. The flap 1020 can be used to manipulate the sealing layer 1007 and provides flexibility to the user during application of the sealing layer 1007. The absence of adhesive on the conduit body 1005 in region 1024 overlying the flap 1020 (and beyond the flap 1020 as shown in FIG. 12) can also act as an interruption such that peeling of the conduit body 1005 adhesive from the patient's skin does not propagate to the sealing layer 1007.

As described with previous embodiments, the dimensions of the components of the device 1000 can vary and can depend on the location to which the device 1000 will be adhered. In some embodiments, the sealing layer 1007 can be between about 2 inches by 7 inches, or between about 3 inches by about 5 inches. The conduit body 1005 can have a length configured so that the proximal port 1125 can be positioned at a location convenient while reducing interference to adjuvant therapies such as offloading devices such as an orthotic, walking boot or total contact cast. For example, the distal aperture 1115 of the sealing layer 1007 may be positioned on the dorsum of the foot for treating a plantar surface wound and the conduit body 1005 may have a length between about 100 mm to about 250 mm such that the proximal port 1125 is positioned in a location remote from the dorsum of the foot. The conduit body 1005 may be thin enough such that it doesn't cause or otherwise reduces excess pressure, but may be thick enough such that there is enough free space to conduct negative pressure through the conduit body 1005. In some embodiments, the thickness of the conduit body 1005 may be in the range of about 1 mm to about 15 mm, about 2 mm to about 12 mm, about 3 mm to about 10 mm, about 5 mm to about 8 mm, or about 6 mm to about 7 mm. In some embodiments, the conduit body 1005 is at least about 6 mm. The conduit body 1005 may have a width that provides for the pressure to be spread out as much as possible, but not so wide as to make the device difficult to handle. In some variations, the width of the conduit body 1005 may be in the range of about 5 mm to about 50 mm, about 10 mm to about 40 mm, about 20 mm to about 30 mm, or about 25 mm to about 35 mm. The conduit body 1005 can also have a width that varies along its length. For example, the width of the conduit body 1005 can taper as it nears the sealing layer 1007. The length of the conduit body may be in the range of about 50 mm to about 500 mm, about 120 mm to about 400 mm, about 150 mm to about 300 mm, about 200 mm to about 300 mm, or about 220 mm to about 250 mm. It should be appreciated that dimensions of the components provided herein are for example and can be longer, shorter, wider, narrower etc. depending on the anatomy to which they may be applied.

As noted above, some embodiments described herein may be used for the treatment of a foot, and in particular, for the treatment of wounds located on a plantar surface of a foot. In these embodiments, it may be desirable to utilize negative pressure wound dressings configured to ameliorate pressure points on the bottom of the foot that would otherwise be exacerbated by traditional negative pressure wound dressings. These pressure points may result from protruding structures of the wound dressing, e.g. a port connector, and/or may result from the relative rigidity of the materials, regardless of the degree of protrusion. In one particular example, at times it may be beneficial to bridge a dressing located on a plantar surface of a foot onto the top (dorsum) of the foot and position any port/tubing transitions at that area, where pressure points are less of a concern. Alternatively, it may be beneficial to bridge the dressing to a point higher on the patient's leg, such as to the calf. In the former case, where the dressing is bridged to the dorsum of the foot, it may be beneficial in some embodiments to secure the bridge, i.e. by adhesion, to the dorsal surface, as this may minimize rubbing or other discomfort if the patient is wearing an offloading appliance or other footwear. In the later case, where the dressing is bridged to a higher point on the calf, it may be more favorable not to adhere the dressing to the patient, as the two points of possible adhesion (plantar surface of foot and point on patient's leg) are separated by a the patient's ankle, which is an articulation point. Having an interposed joint underlying different regions of a dressing and bridge may cause occlusion, protrusion, discomfort and/or undesirable stretching of the dressing. Also, in the case of having the bridge on a point on the patient's leg (as opposed to the dorsum of the foot), there may be less likelihood that the proximal end of a bridging conduit may be located under a restrictive covering over (such as a shoe), so in many cases the risk of discomfort of not being adhered is less. In other examples, however, a patient may be wearing elastic or pneumatic compression stockings or boots, or have other reasons where it may be preferable to adhere the bridge to the underlying tissue or skin. Thus, it may be desirable to configure a bridge device with an adhesive that is protected by a release layer comprising a padded or resilient, non-adhesive material that may be optionally removed if skin adhesion is desired, but which provides a padded or resilient skin contact surface if left intact with the adhesive.

Figure 13B:
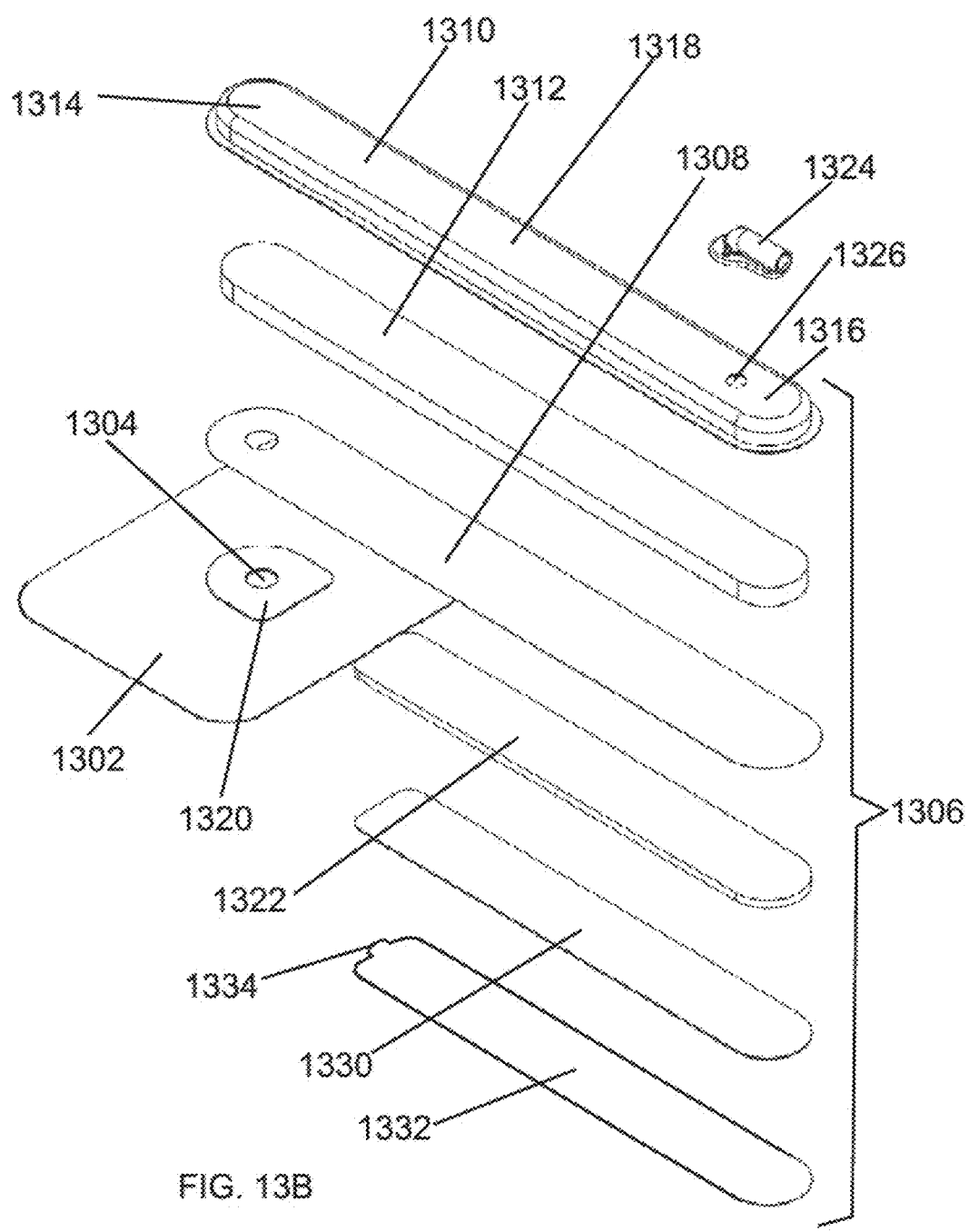
FIG. 13B is an exploded component view of the device in FIG. 13A.

FIGS. 13A and 13B depict another variant of a bridging device 1300, comprising a wound cover 1302, which in turn comprises a substantially airtight polymeric layer or material sufficient to maintain a reduced pressure environment, and a hydrocolloid or other adhesive layer (not shown) configured to provide a substantially airtight seal between the polymeric layer and the skin or tissue surrounding the treatment area. The wound cover 1302 further comprises an opening 1304, over which is placed a bridge section 1306, such that the interior of the bridge section 1306 is in fluid communication with the space immediately below the opening 1304 in the wound cover 1302. The wound cover 1302 and the bridge section 1306 may be attached in an airtight manner by any of a variety of processes described herein, but in the particular embodiment depicted in FIG. 13B, a piece of double-sided airtight tape 1320 is used around the opening 1304. The bridge section 1306 may comprise a unibody tubular structure, or may comprise two or more polyurethane structures which are sealably coupled together, e.g. a bottom bridge layer 1308 and top bridge layer 1310. As disclosed above, the two polyurethane layers may be sealed together along a perimeter by any means known in the art, e.g.

radiofrequency welding or an adhesive, to form an internal cavity. Located in the cavity of the bridge section 1306, a resilient support structure 1312, including one or more pieces of open-cell reticulated foam, or any other porous material as mentioned previously which can conduct negative pressure. In the particular embodiment depicted in FIGS. 13A and 13B, the bridge section 1306 comprises rounded ends 1314, 1316 with a midsection 1318 comprising a uniform width, but in other variations, the bridge section may comprise other shapes, e.g. frustoconical, ellipsoidal or oval, or otherwise tapered. The dimensions of the bridge section 1306 and the resilient support structure 1312 may comprise dimensions and/or materials as described for device 1000 and its conduit body 1005, in addition to other embodiments described herein, e.g. devices 100, 1400, or conduit body 105.

Figure 13C:
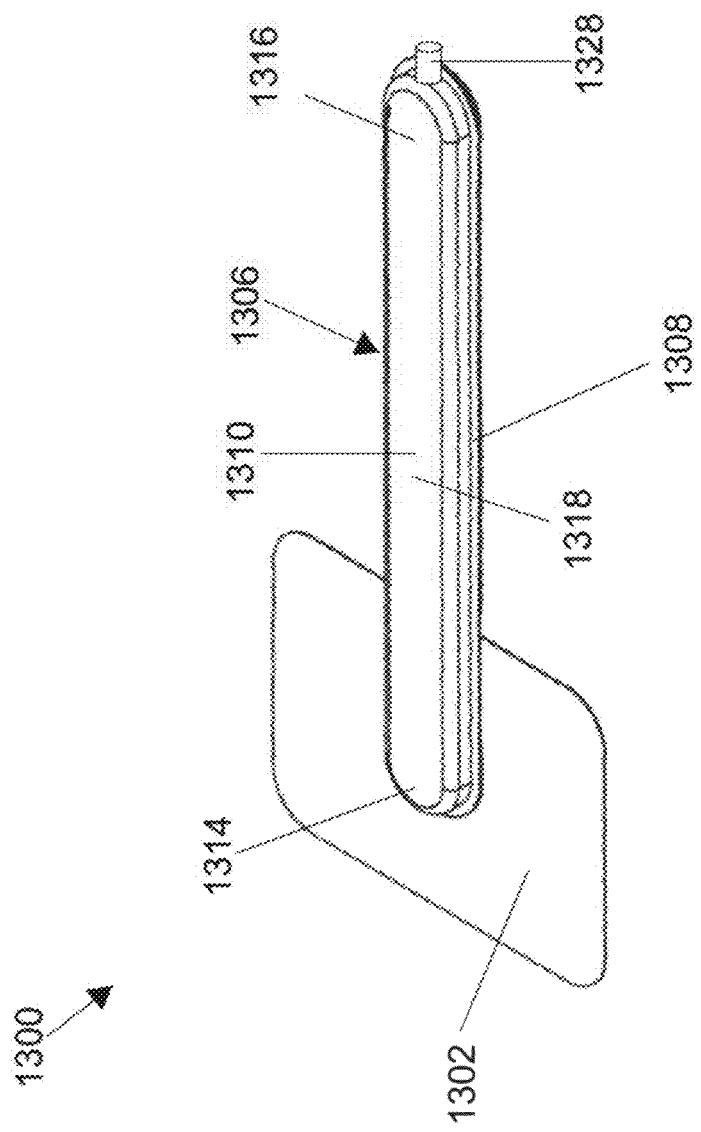
FIG. 13C is a superior perspective view of a variation of the bridge device in FIG. 13A with a tubing connector on a side surface of the proximal end.
Figure 13E:
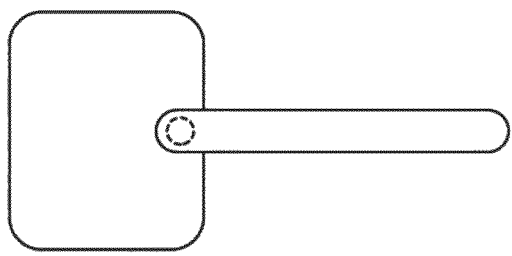
FIGS. 13E to 13J depict various exemplary relative configurations between a wound cover and a bridge section.
Figure 13F:
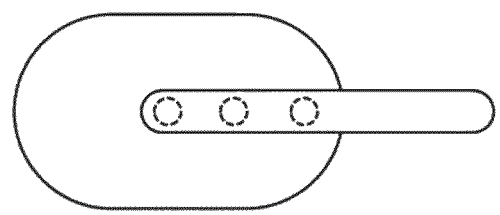
Figure 13G:
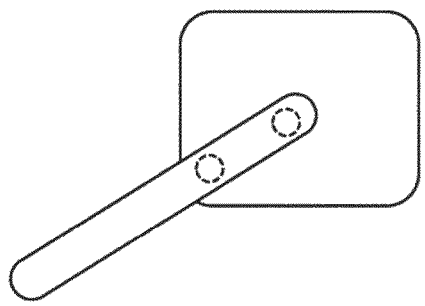
Figure 13H:
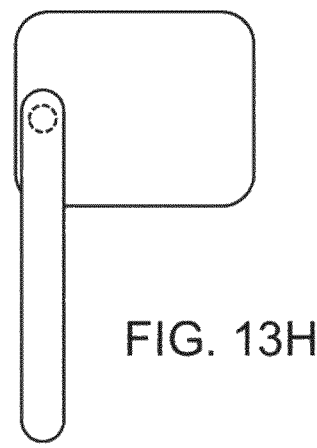
Figure 13I:
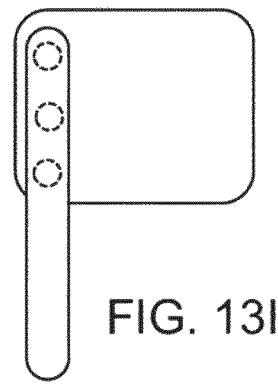
Figure 13J:
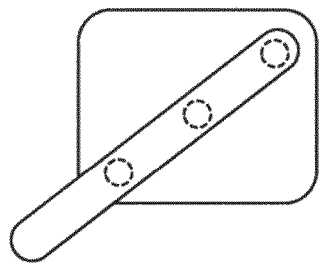

Although the bridge section 1306 in FIGS. 13A and 13B is configured to be in fluid communication with a single center opening of the wound cover 1302, in other variations, the bridge section and wound cover may comprise an off-center fluid communication opening (e.g. oriented anywhere along an edge of the wound cover and outward, as shown in FIG. 13E), and/or the multiple fluid communication openings may be provided between the bridge section and wound cover, along the overlapping length of the bridge section (e.g. FIG. 13F). The relative orientation of the bridge section with regards to the wound cover in FIGS. 13A and 13B is a radial and orthogonal with regards to the square shape of the wound cover, but in other variations, the bridge section may comprise a radial but non-orthogonal orientation, e.g. from the center of the wound cover to a corner of the wound cover (FIG. 13G), or comprise an orthogonal but non-radial orientation, e.g. from the center of one edge to an adjacent cover corner (FIG. 13H), or from one corner to an adjacent corner (FIG. 13I). Other orientations are also contemplated, e.g. corner to non-adjacent corner (FIG. 13J), as well as non-linear. Also, in some embodiments, the bottom layer of the bridge section may be integrally formed with the wound cover.

In embodiments where the bridge section comprises multiple structures sealed together, components such as the bottom bridge layer and top bridge layer may comprise generally planar sheets, but in some further variations, one or more components may comprise non-planar configurations when in an unbiased state, other otherwise not subjected to forces acting upon it. For example, in the embodiment depicted in FIG. 13B, top bridge layer 1310 may be injection molded, or heat or vacuum formed into a non-planar shape, e.g. a recess or open cavity configured to receive the resilient support structure 1312. The bottom and top bridge layers may comprise the same or different materials, and the same or different thickness. Prior to vacuum forming the layers, if any, the material may comprise a thickness of about 0.1 mm to about 0.2 mm, and may comprise polyurethane, polyethylene, or any of a variety of other polymeric materials. The recess or open cavity may have a depth that slightly larger or smaller than the thickness of the resilient support structure 1312. In some variations, the recess is about 0.5 mm to about 2 mm greater than the thickness of the support structure 1312, while in other variations, the recess is about 0.5 mm to about 1.5 mm, about 1 mm to about 2 mm, or about 1.5 mm to about 2 mm larger, for example. In some variations, the recess or cavity may comprise an absolute depth of about 4 mm to about 15 mm or more, sometimes about 6 mm to about 12 mm, or about 8 mm to about 10 mm. In some variations, use of one or more pre-formed non-planar structures may reduce the dead space in the cavity that lies between the resilient support structure 1312 and the bottom and top bridge layers 1308 and 1310 when the bridge conduit is at ambient pressure. In embodiments comprising manual vacuum systems or vacuum systems of limited vacuum capacity, the reduced dead space may permit such systems to provide a longer duration of use before replacement or recharge of the vacuum source, as the lateral dead space may collapse anyway upon the application of reduced pressure, and therefore may not function as part of the effective conduit volume for conveying reduced pressure.

The bottom layer 1308 of the bridge section 1306 may further comprises a soft padding 1322 such as foam, which is not in fluid communication with the interior of the bridge. When negative pressure is applied to the system, the foam in the interior of the bridge will compress and harden; however the foam on the exterior of the bridge which is not in fluid communication with the interior will remain soft and pliable, enhancing the ability of the dressing to reduce pressure points on the patient. In some variations, the thickness of the padding 1322 may be in the range of about 1 mm to about 10 mm, about 1 mm to about 8 mm, about 2 mm to about 5 mm, about 2 mm to about 4 mm, about 2 mm to about 3 mm.

Typically, but not always, the greatest pressure point of the bridge device or bridge section 1306 is where the traditional suction tubing attaches to it. The attachment of the tubing may be configured such that the tubing is generally parallel to the plane of the dressing or bridge and terminates in an elastomeric port structure 1324, as depicted in FIGS. 13A and 13B. This port structure 1324 may be positioned over an opening 1326 in the top layer 1310 of the bridge section 1306 and then bends the fluid path 90 degrees such that the tubing is in fluid communication with the interior of the bridge. In another embodiment, depicted in FIG. 13C, the tubing may run parallel to the plane of the dressing 1302 and bridge section 1306, and terminates directly into a side connector 1328 located in the side surface of the proximal end 1316 of the bridge sections 1306, where it is welded or otherwise affixed in an airtight manner to the bridge sections 1306. In this embodiment, there is no bend in the fluid path of the connector 1328. Also, in this particular embodiment, the base of the connector 1328 is attached to the formed top layer 1310 of the bridge section 1306, but in other variations, the base of the connector may attached to both layers 1308, 1310.

As shown in FIG. 13B, in some further variations, an adhesive 1330, such as a low-tack non-traumatic silicone, hydrocolloid or acrylic layer, may be provided on the bottom of the padding 1322, along with a release liner 1332. In some variations, the release liner 1332 may be a typical release liner that is generally configured to protect the adhesive until ready for use or to provide some rigidity to the underlying structure, and may comprise a protruding flap or tab 1334 to facilitate removal. In some variations, the flap or tab 1334 may be smaller or larger (e.g. the same width as the rest of the release liner 1332) than what is depicted in FIG. 13B, and may be optionally pre-folded over itself. Although the embodiment depicted in FIG. 13B depicts a tab 1334 as located at the distal end 1314 of the bridge section 1306, in other variations, the tab may be located at the proximal end 1316 or between the ends 1314, 1316. FIG. 13D depicts the fully constructed device 1300, along with a tubing 1336, check valve 1338 and tubing connector 1340 attached to the device 1300.

In other variations, however, the release liner 1332, in contrast to typical liners, may comprise a skin-friendly surface or material which, at the clinician's election, may either be removed to expose the adhesive, or left in place to allow the bridge to move relative to the patient's skin. The substrate or material may comprise a soft, resilient materials, such as felt or other woven or non-woven fibrous materials made from polypropylene, rayon, polyethylene terephthalate or acrylic fibers, for example. The material may be a hydrophobic absorbent material or a wicking material that facilitates moisture evaporation via capillary action. The material may possess moisture transport rates greater than about 200 g/m$^2$/day, about 400 g/m$^2$/day, about 1000 g/m$^2$/day or higher.

Figure 14A:
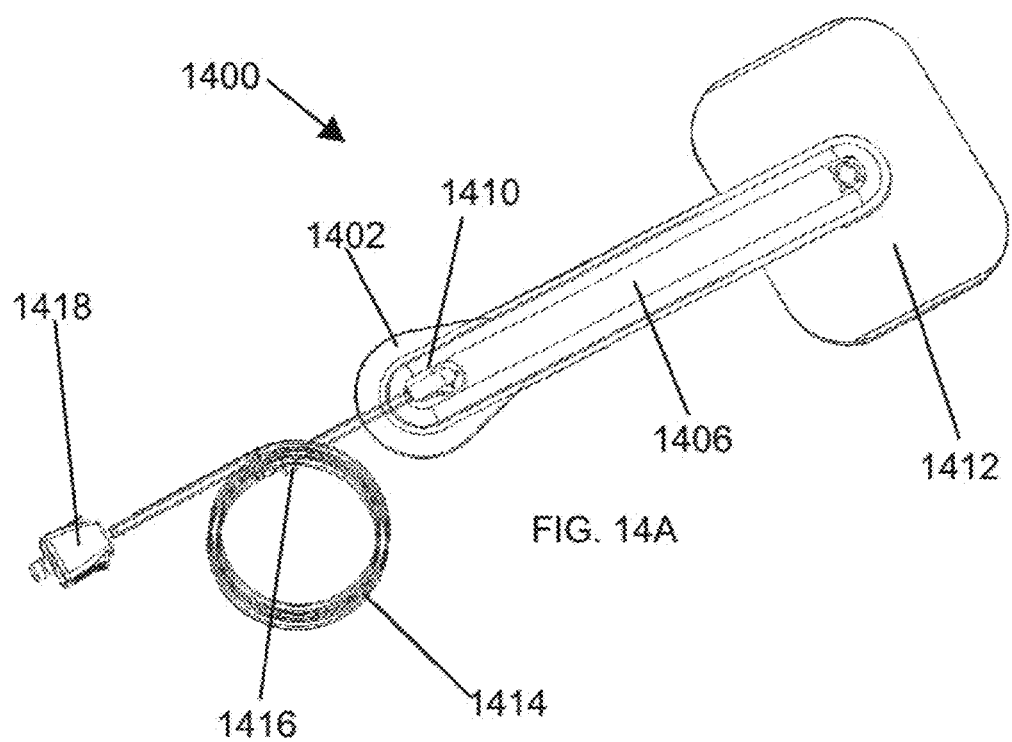
FIGS. 14A and 14B are superior and inferior perspectives of another variant of a bridge attached to a port, tubing and tubing connector.
Figure 14B:
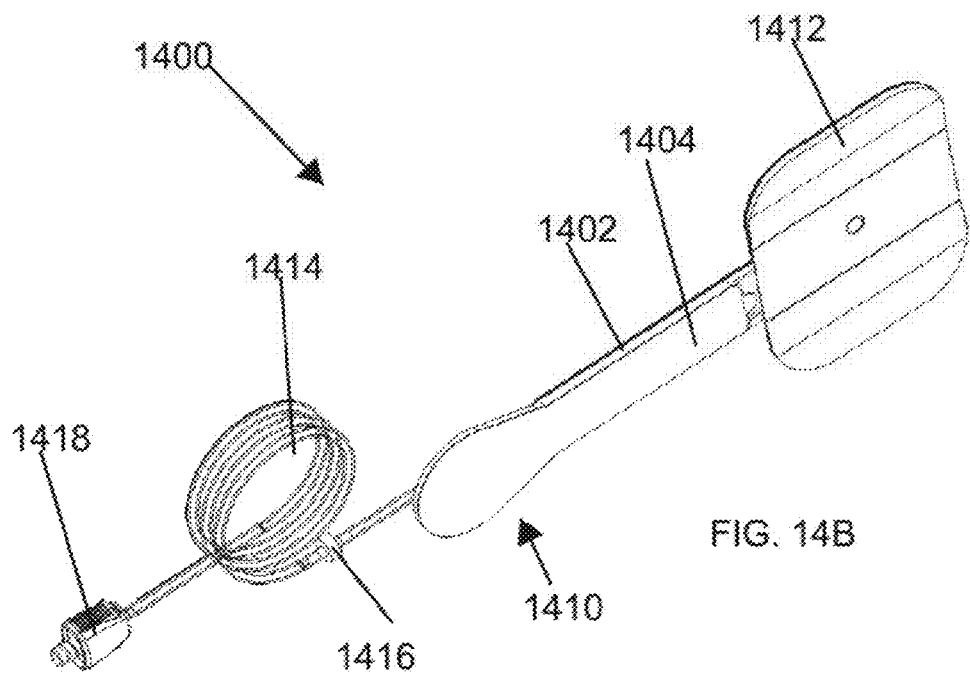

Referring still to the embodiment depicted in FIG. 13B, the padding 1322 (and optional adhesive 1330 and 1332) may comprise dimensions that are at or within the peripheral boundary or edge of the bridge section 1306. In other embodiments, however, such as the device 1400 depicted in FIGS. 14A and 14B, the device 1400 may be similar to device 1300 in construction and in described variations, but also includes a pad 1402 (and optional adhesive and release liner 1404) that comprises dimensions that are larger than the bridge section 1406 in at least one region or dimension. In this particular embodiment, the pad/release liner 1402, 1404 comprises a bulbous or otherwise enlarged proximal end 1410. In some variations, the increased surface area of the pad and release liner 1402, 1404 may provide greater surface protection (if used non-adhesively) or greater adhesion (if used adhesively) at the proximal end 1410 of the bridge section 1406, which may be prone displacement patient movement transmitted through loose tubing 1414, or because it has a relatively smaller surface area than the wound covering 1412. Release liner 1404 may otherwise have any of a variety of configurations as described for release liner 1322 of device 1300. The device 1400 in FIGS. 14A and 14B is also depicted with attached tubing 1414, as well as a check valve 1416 and tubing connector 1418 configured to form an interfit with a vacuum source (not shown). The tubing 1414, check valve 1416 and/or tubing connector 1418 may be attached to the device 1400 at the point of use, or at the point of manufacture. In some variations, a pre-attached tubing connector 1418 may be easier to attach to a vacuum source compared to the act of manually attempting to pass a tubing end over a multi-flanged connector in a manner that provides an airtight seal. The particular connector 1418 depicted herein is a latch-based quick-release connector configured for use with the suction cartridge disclosed in U.S. Pat. No. 8,128,607, which is hereby incorporated by reference in its entirety, but one of skill in the art that any of a variety of connector configurations may be used, e.g. Luer fitting, John Guest quick connector, collet connector, etc. or a customized fitting.

Figure 15A:
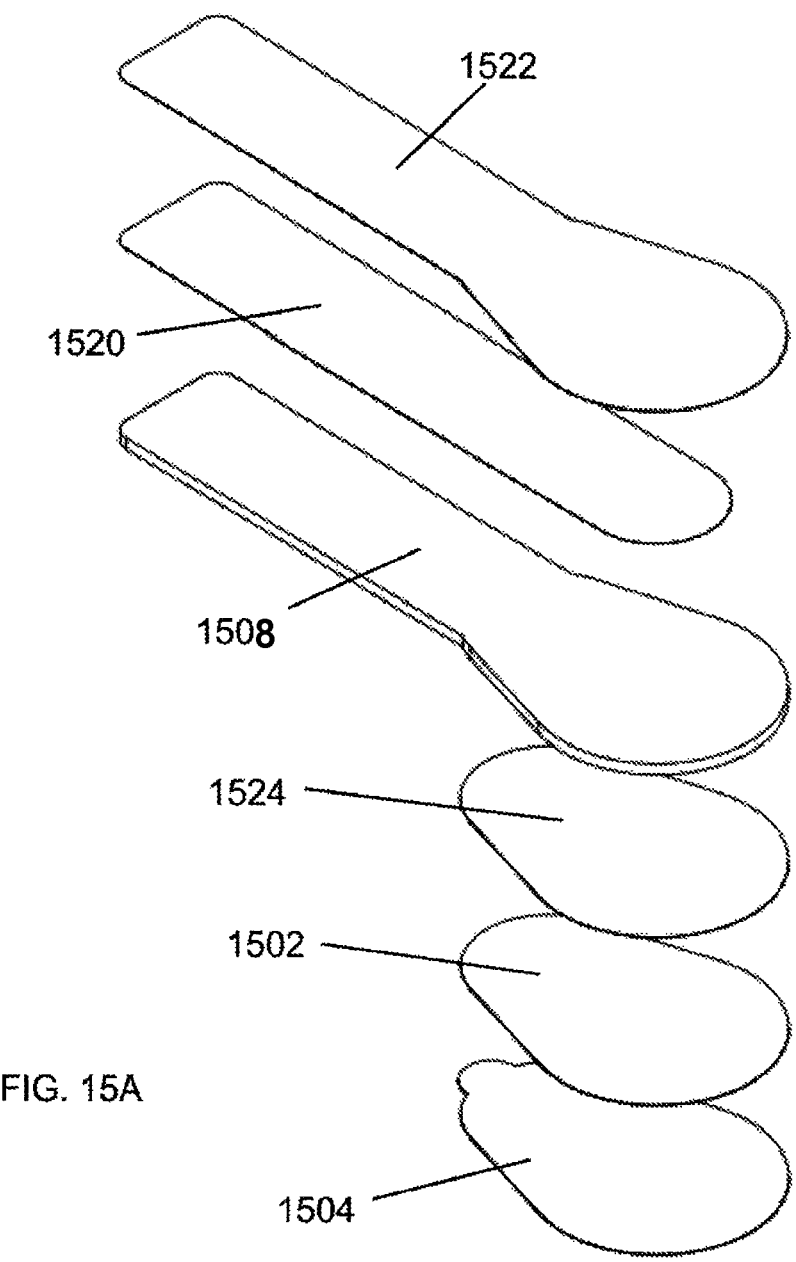
FIG. 15A is an exploded component view of another variant of a bridge device.
Figure 15B:
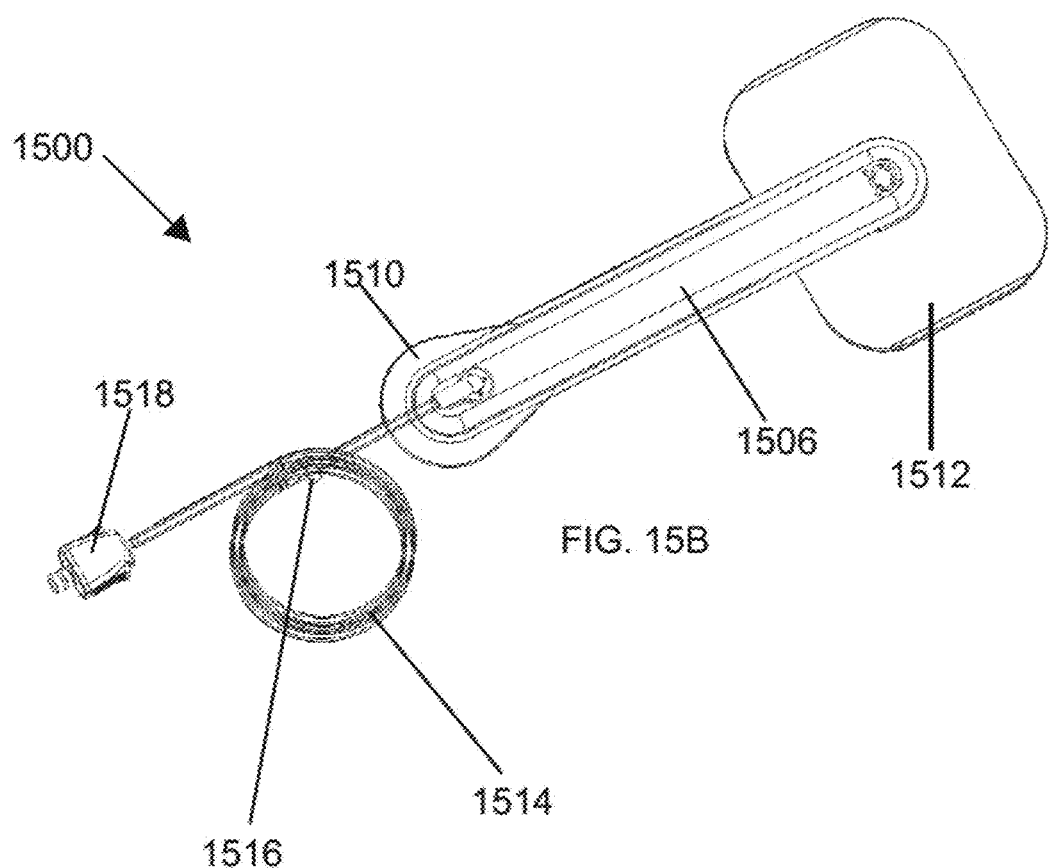
FIGS. 15B and 15C are superior and inferior perspectives of the bridge device of FIG. 15A attached to a port, tubing and tubing connector.
Figure 15C:
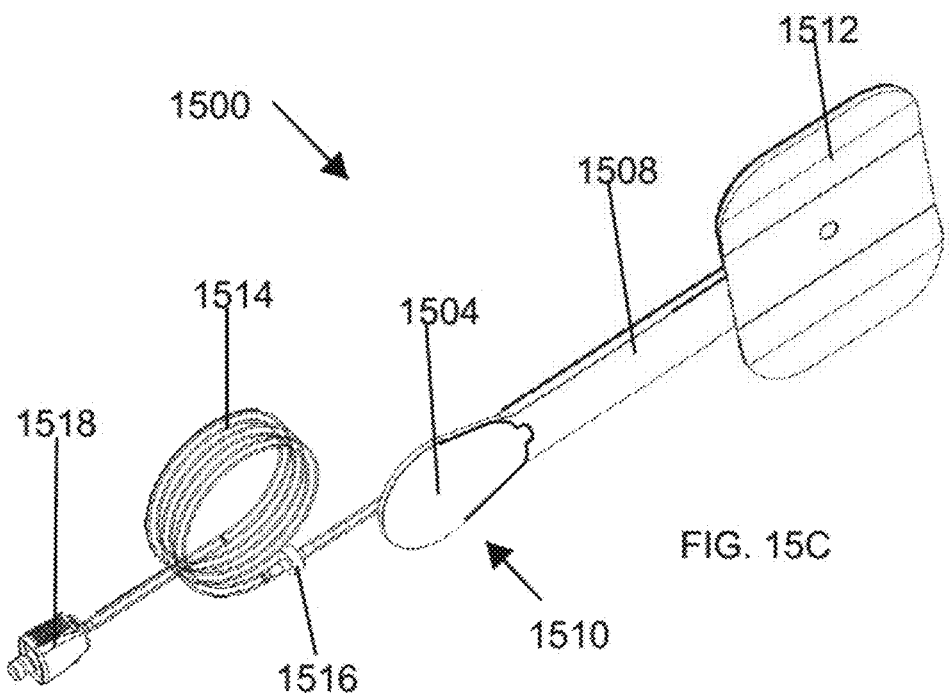

In some other variations of the bridge device, such as the device 1500 depicted in FIGS. 15A to 15C, the device 1500 may be similar to devices 1300 and 1400 in materials, construction and in described variations, but the adhesive layer 1502 (and release liner 1504) of the bridge section 1506 may comprise a region or surface area that is less than the entire area of the pad 1508. In the depicted example, the adhesive layer 1502 is generally limited to the proximal end, or enlarged region 1510 of the pad 1508, but one of skill in the art will understand that the location and/or size may be varied along the length of the pad, and that multiple separate or contiguous may be provided, each with independent release liners to provide selective use of the provided adhesive regions if any. Release liner 1504 may otherwise have any of a variety of configurations as described for release liner 1332 of device 1300, or liner 1404 of device 1400. The device 1500 in FIGS. 15B and 15C is also depicted with attached wound cover 1512, tubing 1514, as well as a check valve 1516 and tubing connector 1518 configured to form an interfit with a vacuum source (not shown).

In some variations, the pad may be attached at the point of use, or may be otherwise supplied as a separate product ready for attachment at the point of manufacture. As shown in FIG. 15A, for example, the pad 1508 may be provided with an upper adhesive layer 1520 that is configured for attachment to an undersurface of a bridging product, e.g. bridge section 1506 of device 1500. Because the bridge section 1506 of device 1500 is narrower at its proximal end than the pad 1508, the adhesive layer 1520 need not comprise an enlarged proximal end. This upper adhesive layer 1520 may also be provided with its own upper release layer 1522, to protect the adhesive layer 1520 until ready for attachment. However, upper release layer 1522 need not comprise any skin-protective characteristics, as described for release liners 1332, 1404 and 1504. In some variations, as shown in FIG. 15A, one or more tie layers 1524 may be provided to facilitate adhesion of the skin adhesive layer 1502 to the pad 1508. In the depicted sample, the tie layer may comprise an adhesive such as acrylic, while the skin adhesive layer 1502 may comprise a low-tack adhesive as described elsewhere. This tie layer is not limited to the smaller adhesive layer embodiment of device 1500, and may also be provided for the adhesive layers of device 1300 and 1400, as well as other embodiments described herein.

Although the embodiments depicted in FIGS. 13A to 15C include devices with bridge sections that have either a generally uniform width along their length, or a generally uniform width in the middle and distally, but with an enlarged proximal end, in other variations, the bridging section may generally taper along its length. Such dressings may be beneficial when treating tissue located on toes or fingers. In other variations, however, smaller, uniform width conduits may also provided for use on toes or fingers. The wound cover may also be configured for use on the fingers or toes, which may include a smaller size as well as a different shape that is better suited for wrapping around a digit, or at the end of a digit.

Figure 16A:
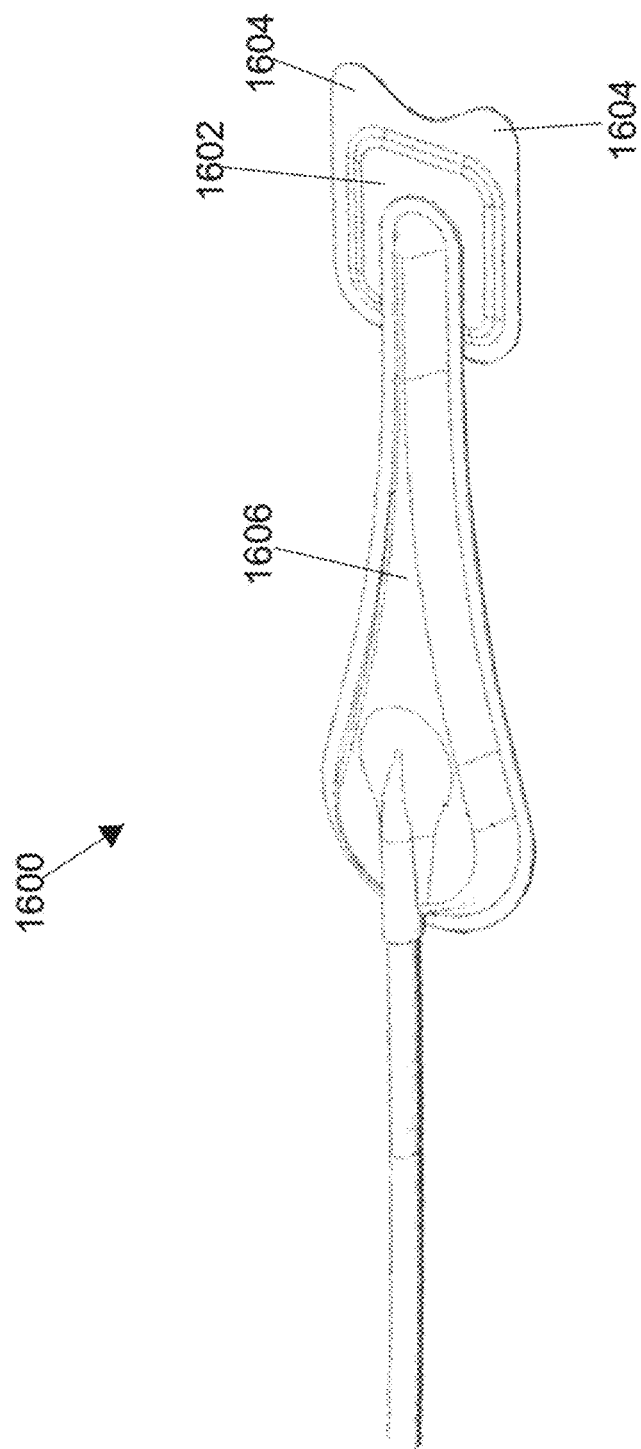
FIGS. 16A and 16B are superior perspective and inferior views of still another variant of a bridge device configured for use on a digit.
Figure 16B:
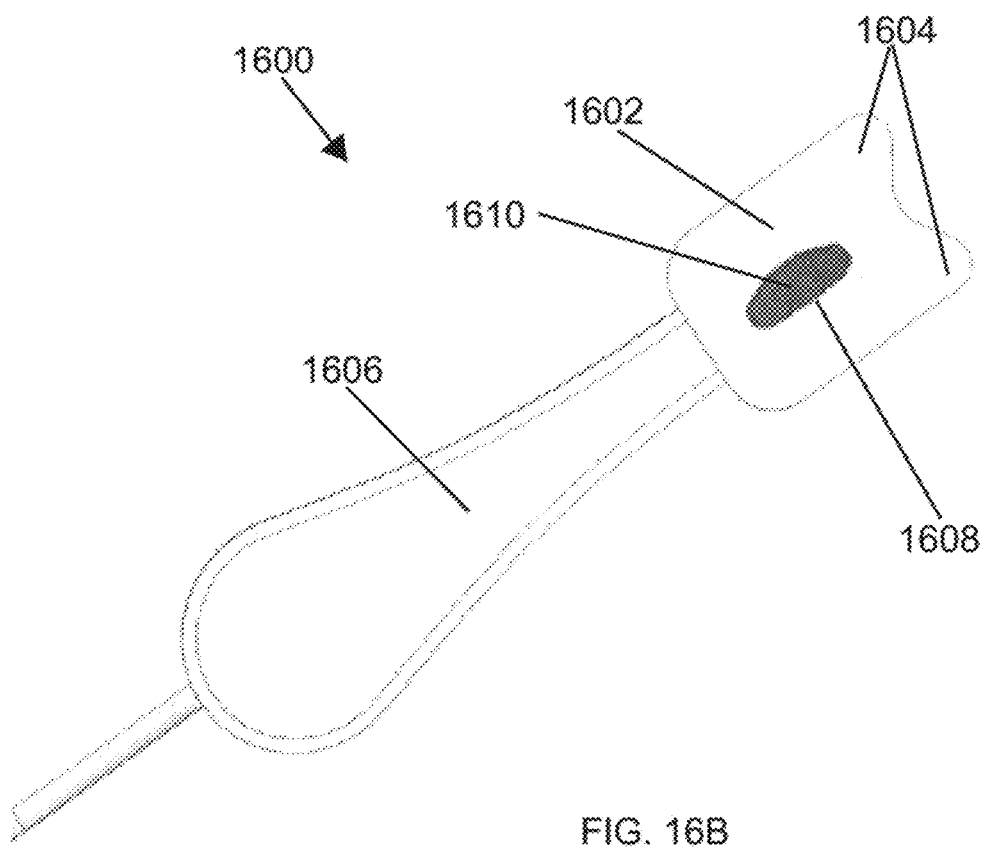

For example, for a regular bridge dressing, the base layer may have dimensions of about 14 cm by about 11 cm, and the bridge may be about 22 cm long and about 2.5 cm wide. In contrast, the device 1600 depicted in FIGS. 16A and 16B is tailored to, but not limited to, use in the toe, whereby the wound cover 1602 may have reduced dimensions, e.g. 8 cm×5 cm, while the bridge section 1606 may also be smaller, e.g. about 15 cm long and about 1.5 cm wide. The wound cover 1602 in this embodiment may be shaped to facilitate forming seals around highly curved surfaces, such as having re-curved edges or "butterfly" lobes 1604 on one or two opposing ends of the wound cover 1602. The bridge section 1606 and wound cover 1602 may otherwise comprise similar materials and construction as described elsewhere herein, including the adhesive and release layers described for devices 1300, 1400, 1500 and others herein.

In some variations, due to surface area constraints of a digit, there may not be sufficient space to provide an intervening contact layer or material, e.g. gauze or foam, between the wound cover and the treated tissue. In such instances, the digit treatment device may comprise a distal opening 1608 between the bridge section 1606 and the wound cover 1602 that is sufficiently large so that the conduit material 1610 is sufficiently exposed and may function as the contact layer. In some further variations, the conduit material 1610 may protrude from the distal opening 1608 or otherwise lie below the wound cover 1602, which may further facilitate tissue contact. In some further variations, the distal end of the conduit material 1610 may be larger than the distal opening 1608 of the wound cover 1602. This larger size may facilitate placement of the device 1600 by allowing the device 1600 to be placed such that the distal opening 1608 of the wound cover 1602 does not need to lie directly over the wound. The clinician may thus place the distal opening 1608 of the wound cover 1602 at a point away from the wound, as long as the conduit material 1610 that lies underneath the wound cover 1602 is oriented such that it touches the wound. In this manner, the distal opening 1608 of the wound cover 1602 may be placed in a convenient location, such as the top of the big toe, and the conduit material 1610 under the wound cover 1602 may be extended to reach a wound in a less convenient location, such as the tip of the toe. In some embodiments, the bottom surface of the wound cover 1602 may comprise a sheet material which will protect the skin underneath the conduit from moisture that would accumulate due to the presence of the conduit section, e.g. rayon or other non-adherent wicking layer.

In some further variations, the wound cover may be further shaped such that it has three-dimensional structure, instead of being substantially planar. Such base layer shapes may include domes, paraboloids or closed cylinders, for example. In some variations, a three-dimensional shape may be provided with the adhesive (hydrocolloid or other) is present on the concave surface of the shape. As a more concave shape (i.e. the base layer) is conformed to an even more convex shape, of a digit or equivalently less concave shape (i.e. the body), the more concave shape may be configured with a structure and/or a material that stretches out in order to assume the same contours as the less or more concave shape. This stretching may mitigate wrinkling of the wound cover which might lead to leak paths. In the device 1700 depicted in FIGS. 17A and 17B, for example, the wound cover 1702 comprises a substantially cylindrical cavity 1704 with a proximal opening 1706 and a closed distal end 1708, which is configured for receiving a finger or toe. A proximal flap or lobe 1710, which may or may not be contiguous with the edge of the proximal opening 1706, may be provided. This proximal flap or lobe 1710 may provide additional surface area to secure the bridge section 1712 to the wound cover 1702 during manufacturing, and/or to provide additional material to wrap around and secure the device 1700 to the digit. The bridge section 1712 and wound cover 1702 may otherwise comprise similar materials and construction as described elsewhere herein, including the adhesive and release layers described for devices 1300, 1400, 1500, 1600 and others herein.

Figure 18:
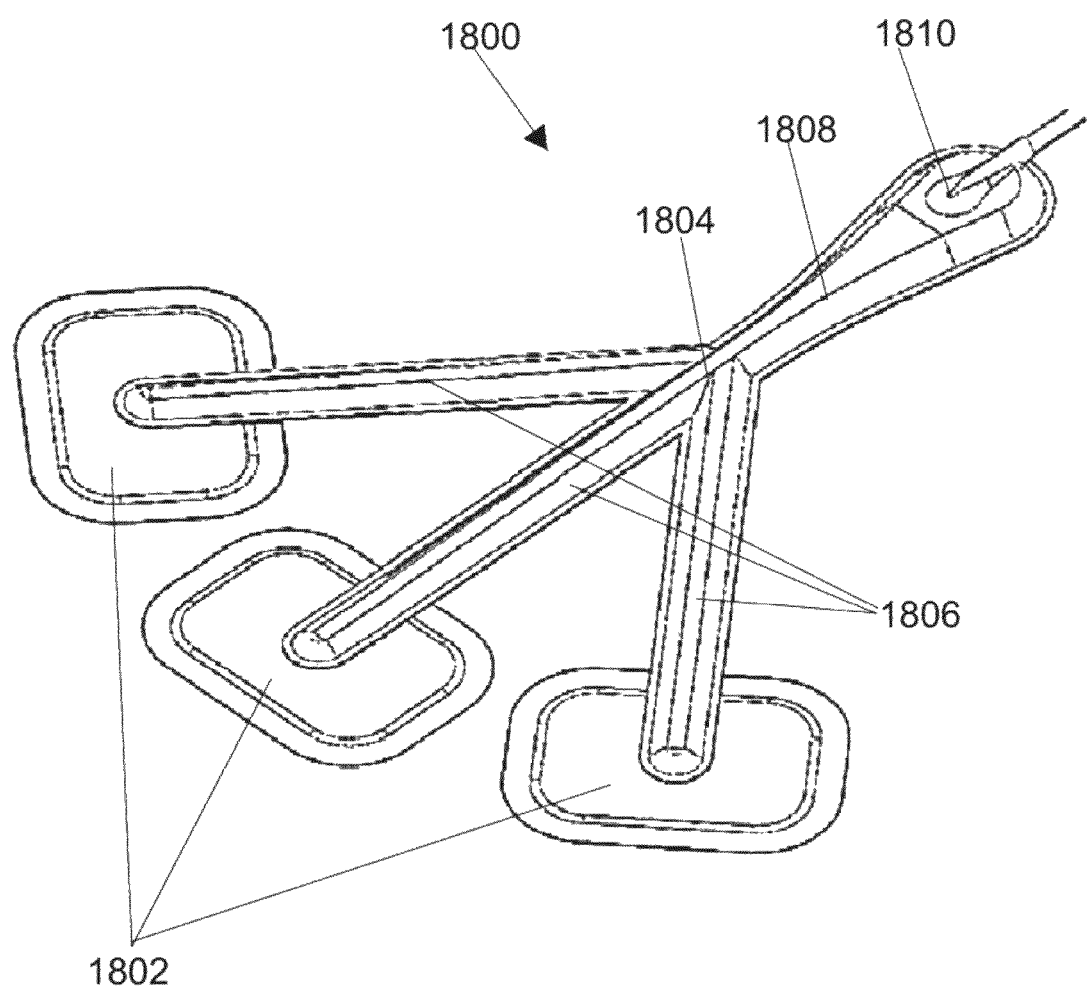
FIG. 18 is a superior perspective view of a branching device.

Although the bridging devices described above are configured to provide a bridge between a treatment site and a more described tubing attachment location, in other embodiments, the bridge device may be configured to provide a bridge between multiple treatment sites and one or more vacuum sources. The device 1800 illustrated in FIG. 18, is an example of a multi-site treatment device with multiple wound covers 1802, each in fluid communication with a hub 1804 via secondary conduit segments 1806. Although each of the depicted wound covers 1802 is identical in size, shape and angular spacing, in other variations, one or more of the wound covers may comprise a different size, shape or spacing. Also, the secondary conduit segments 1806 are depicted as having the same general configuration, size and shape, but in other variations, one or more of the conduit segments may comprise a different size or shape. Furthermore, the conduit segments 1806 are depicted as converging to a common location of the hub 1804, but in other variations, the conduit segments 1806 may attach to different locations along the hub 1804. This particular embodiment also depicts a primary conduit segment 1808 proximal to the hub 1804, to which a tubing connector 1810 is attached and spaced away from most proximal branch of a secondary conduit segments 1806. In other embodiments, however, the tubing connector may be at the intersection of the most proximal secondary conduit segments 1806, or even distal to the most proximal secondary conduit segments 1806. For example, FIG. 19 depicts one variation of a device 1900 comprising two wound covers 1902 located 180 degrees apart and equidistant from a hub 1904 and tubing connector 1906. In other variations, the covers 1902 may be located at a different separation angle, e.g. about 15 degrees apart, about 30 degrees apart, about 45 degrees apart, about 60 degrees apart, about 75 degrees apart, about 90 degrees apart, about 105 degrees apart, about 120 degrees apart, about 135 degrees apart, about 150 degrees apart, or about 165 degrees apart. This particular hub 1904 also comprises an enlarged pad 1908 with a tabbed release liner 1910, but in other variations, the pad may not extend from the edges of the conduit 1912. Also, in other examples, the tubing connector 1906 may be located closer to one of the wound covers 1902. Furthermore, although this particular example depicts three secondary conduit segments 1806, in other variations, there may be two, three, four or any number of such bridge conduits emanating from the central hub. Alternatively, the structural arrangement could be more branched, such that there is a single bridge conduit that splits into multiple conduits at some point along its length. Except as above, the materials, constructions and variations of the above embodiment may be the same as described for other embodiments, herein, including but not limited to devices 1300, 1400, 1500, 1600, 1700 and others herein. As depicted in FIG. 18, at least the branch point of two units are equidistant from the two wounds that they are treating; however in cases where this is difficult to achieve, the branch that is too long may be "z-folded" against itself to reduce its effective length. In still other variations, the devices may comprise accordion-like regions which may length and/or angle adjustment of one or more of the secondary conduit segments 1806.

One potential benefit of the branching conduit device is that they permit the treatment of multiple regions without the need for rigid components, such as Y-connectors and affords all of the advantages of bridging. If any number of the plurality of the individual conduits is not to be used, it is possible to cut it from the hub or the branched structure and seal the end to prevent or resist vacuum leakage. The cut branch may be sealed using clips, clamps and/or adhesive sheets or adhesives coatings.

In some procedures where the above embodiments and variations are employed, to reduce waste and/or prolong treatment duration before exchanging or otherwise replenishing the vacuum source, the user may externally compress the devices to evacuate as much residual air in the device, before attaching a vacuum source.

It should be appreciated that one or more of the components of any of the systems and devices described herein can include an additive(s) such as antimicrobials, anti-bacterials, antibiotics, antivirals, antifungals, antiseptics, anti-inflammatories, anesthetics and other therapies. One or more of the components of the system can also include anti-clotting materials to help mitigate issues with blockage within the long conduit structures.

While a number of embodiments have been shown and described herein, one of skill in the art will understand that these embodiments are provided by way of example only. Numerous variations, changes, and substitutions may be made those skilled in the art without departing from the invention. It should be understood that various alternatives to the embodiments described herein may also be employed. It is intended that the following claims define the scope of the invention and that methods and structures within the scope of these claims and their equivalents be covered thereby. For all of the embodiments described herein, the steps of the methods need not be performed sequentially.

What is claimed as new and desired to be protected is:

1. An elongate conduit structure for providing reduced pressure therapy to a tissue site, the elongate conduit structure comprising:
    an upper surface and a lower surface each extending along a longitudinal length of the elongate conduit structure;
    a longitudinal passageway extending along the longitudinal length of the elongate conduit structure and between the upper surface and the lower surface;
    an inlet opening located in the lower surface;
    an outlet opening located in the upper surface;
    a support structure defining parallel channels through the longitudinal passageway, wherein each of the parallel channels extends from the inlet opening to the outlet opening, and wherein the support structure comprises one or more elongate ribs coupled to at least one of the upper surface or the lower surface;
    a port coupled to the upper surface and in fluid communication with the outlet opening; and
    a first tissue protection structure configured to be positioned below the lower surface of the elongate conduit structure.

2. The elongate conduit structure of claim 1, further comprising:
    an adhesive structure coupled to at least one of the lower surface of the elongate conduit structure and the first tissue protection structure; and
    a release liner adhered to the adhesive structure, wherein the release liner comprises a release surface in contact with the adhesive structure, and wherein a second tissue protection structure is on an opposite surface from the release surface.

3. The elongate conduit structure of claim 2, wherein the release liner extends beyond an edge of the adhesive structure.

4. The elongate conduit structure of claim 2, wherein the first tissue protection structure comprises a different material than the second tissue protection structure.

5. The elongate conduit structure of claim 2, wherein the first tissue protection structure comprises a foam.

6. The elongate conduit structure of claim 2, wherein the second tissue protection structure comprises a woven material.

7. The elongate conduit structure of claim 1, wherein the support structure comprises a foam.

8. The elongate conduit structure of claim 2, wherein the adhesive structure is attached to the first tissue protection structure.

9. The elongate conduit structure of claim 1, wherein the inlet opening is located at a distal region of the elongate conduit structure.

10. The elongate conduit structure of claim 9, wherein the outlet opening is located at a proximal region of the elongate conduit structure.

11. The elongate conduit structure of claim 9, wherein the outlet opening is located between a proximal region of the elongate conduit structure and the distal region of the elongate conduit structure.

12. The elongate conduit structure of claim 2, wherein the upper surface and the lower surface are integrally formed.

13. The elongate conduit structure of claim 2, wherein the upper surface and the lower surface form a seam along an outer perimeter of the elongate conduit structure.

14. The elongate conduit structure of claim 13, wherein the upper surface comprises a non-planar, vacuum formed polymeric structure, and wherein the lower surface comprises a planar polymeric structure.

15. The elongate conduit structure of claim 2, wherein the dressing is attached to the elongate conduit structure at the inlet opening.

16. The elongate conduit structure of claim 1, wherein an edge of the dressing is aligned with an edge of the first tissue protection structure.

17. The elongate conduit structure of claim 1, wherein the dressing does not overlap with the first tissue protection structure.

18. The elongate conduit structure of claim 1, wherein the first tissue protection structure comprises a lateral perimeter portion that extends beyond a lateral perimeter of the elongate conduit structure.

19. A method to treat tissue, the method comprising:
    attaching at least one wound cover having an elongated conduit to a treatment site, wherein the elongated conduit is pre-coupled between the at least one wound cover and a tube that extends to a vacuum source, the elongated conduit comprising:
        an upper surface and a lower surface each extending along a longitudinal length of the elongated conduit,
        a longitudinal passageway that extends along the longitudinal length of the elongated conduit and between the upper surface and the lower surface,
        an inlet opening located in the lower surface,
        an outlet opening located in the upper surface,
        a support structure defining parallel channels through the longitudinal passageway, wherein each of the parallel channels extends from the inlet opening to the outlet opening, and wherein the support structure comprises one or more elongate ribs coupled to at least one of the upper surface or the lower surface,
        a port coupled to the upper surface and in fluid communication with the outlet opening, and
        a first tissue protection structure configured to be positioned below the lower surface of the elongated conduit;
    externally compressing the elongated conduit;
    attaching the vacuum source to the elongated conduit; and
    activating the vacuum source after externally compressing the elongated conduit.

20. The method of claim 19, further comprising maintaining at least some external compression of the elongated conduit while activating the vacuum source.

21. The elongate conduit structure of claim 1, further comprising a support configured to maintain fluid communication between the inlet opening and the parallel channels under an external force.

22. The elongate conduit structure of claim 1, wherein the first tissue protection structure is porous.

23. The elongate conduit structure of claim 2, wherein the second tissue protection structure is porous.

24. The elongate conduit structure of claim 1, wherein the support structure maintains the parallel channels in a parallel configuration through the longitudinal passageway.

25. The method of claim 19, wherein the upper surface and the lower surface are impermeable.

* * * * *